(12) United States Patent
Namkung et al.

(10) Patent No.: US 11,274,074 B2
(45) Date of Patent: Mar. 15, 2022

(54) PHARMACEUTICAL COMPOSITION FOR ANO1 ANTAGONIST WITH ANTICANCER ACTIVITY

(71) Applicant: INDUSTRY-ACADEMIC COOPERATION FOUNDATION, YONSEI UNIVERSITY, Seoul (KR)

(72) Inventors: Wan Namkung, Incheon (KR); Ik Yon Kim, Seoul (KR); Yohan Seo, Jeollabuk-do (KR); Jin Hwang Kim, Gyeonggi-do (KR)

(73) Assignee: INDUSTRY-ACADEMIC COOPERATION FOUNDATION YONSEI UNIVERSITY, Seoul (KR)

( * ) Notice: Subject to any disclaimer, the term of this patent is extended or adjusted under 35 U.S.C. 154(b) by 105 days.

(21) Appl. No.: 16/574,701

(22) Filed: Sep. 18, 2019

(65) Prior Publication Data
US 2020/0087250 A1    Mar. 19, 2020

(30) Foreign Application Priority Data
Sep. 19, 2018  (KR) .......................... 10-2018-0112056

(51) Int. Cl.
| | | |
|---|---|---|
| *C07C 251/80* | (2006.01) |
| *A61P 35/00* | (2006.01) |
| *C07C 243/18* | (2006.01) |
| *C07D 271/06* | (2006.01) |
| *C07D 307/54* | (2006.01) |
| *C07D 413/04* | (2006.01) |
| *C07D 213/56* | (2006.01) |
| *C07D 263/58* | (2006.01) |
| *C07D 277/54* | (2006.01) |
| *A61K 9/20* | (2006.01) |
| *A61K 9/48* | (2006.01) |
| *A61K 9/00* | (2006.01) |
| *C07C 233/29* | (2006.01) |

(52) U.S. Cl.
CPC .......... *C07C 251/80* (2013.01); *A61K 9/0095* (2013.01); *A61K 9/20* (2013.01); *A61K 9/48* (2013.01); *A61P 35/00* (2018.01); *C07C 233/29* (2013.01); *C07C 243/18* (2013.01); *C07D 213/56* (2013.01); *C07D 263/58* (2013.01); *C07D 271/06* (2013.01); *C07D 277/54* (2013.01); *C07D 307/54* (2013.01); *C07D 413/04* (2013.01)

(58) Field of Classification Search
CPC ... C07C 251/80; C07C 251/72; C07C 251/74; C07C 251/78; C07D 307/52; C07D 213/53; A61P 35/00
See application file for complete search history.

(56) References Cited

U.S. PATENT DOCUMENTS

2013/0225610 A1* 8/2013 Hansen ................ C07D 487/04
514/262.1

FOREIGN PATENT DOCUMENTS

| KR | 1020140112489 | | 9/2014 | |
|---|---|---|---|---|
| KR | 20170019905 | * | 2/2017 | .......... A61K 31/165 |
| KR | 1017195410000 | | 3/2017 | |

OTHER PUBLICATIONS

Germain et al. Bioorg. Med. Chem. Lett. 2012, 22, 3571-3574.*
Patani et al. Chemical Reviews 1996, 96, 3147-3176.*
CAS registry No. RN 328113-75-3, entered STN Mar. 20, 2001.*
CAS registry No. RN 478528-12-0, entered STN Jan. 9, 2003.*
CAS registry No. RN 329020-83-9, entered STN Mar. 27, 2001.*
Seo et al., "Synthesis and biological evaluation of novel Ani9 derivatives as potent and selective ANO1 inhibitors", European Journal of Medicinal Chemistry, vol. 160, 2018, pp. 245-255.
Huang et al., "Calcium-activated chloride channel TMEM16A modulates mucin secretion and airway smooth muscle contraction", vol. 109, No. 40, Oct. 2, 2012, pp. 16354-16359.
Cho et al., "The calcium-activated chloride channel anoctamin 1 acts as a heat sensor in nociceptive neurons", Nature Neuroscience, vol. 15, No. 7, Jul. 2012, pp. 1015-1021.
Wang et al., "Cell-specific mechanisms of TMEM16A Ca2+-activated chloride channel in cancer", Molecular Cancer, vol. 16, No. 152, 2017, pp. 1-17.
Wang et al., "Overexpression of ANO1/TMEM16A, an arterial Ca2+-activated Cl-channel, contributes to spontaneous hypertension", Journal of Molecular and Cellular Cardiology, vol. 82, 2015, pp. 22-32.
Takayama et al., "Pain-enhancing mechanism through interaction between TRPV1 and anoctamin 1 in sensory neurons", Proc. Natl. Acad. Sci., vol. 112, No. 16, Apr. 21, 2015, pp. 5213-5218.
Deba et al., "Anoctamin-1 Cl-channels in nociception: activation by an N-aroylaminothiazole and capsaicin and inhibition by T16A[inh]-A01", Molecular Pain, vol. 11, No. 55, 2015, pp. 2-15.
Pietra et al., "The Ca2+-activated Cl-channel TMEM16B regulates action potential firing and axonal targeting in olfactory sensory neurons", J. Gen Psysiol., vol. 148, No. 4, 2016, pp. 293-311.
Neureither et al., "Impaired Motor Coordination and Learning in Mice Lacking Anoctamin 2 Calcium-Gated Chloride Channels", Cerebellum, vol. 16, 2017, pp. 929-937.
Forrest et al, "Increased TMEM16A-encoded calcium-activated chloride channel activity is associated with pulmonary hypertension", Am J Physiol Cell Physiol, vol. 303, Aug. 20, 2012, pp. C1229-C1243.

* cited by examiner

Primary Examiner — Irina Neagu
(74) Attorney, Agent, or Firm — Duane Morris LLP; Gregory M. Lefkowitz

(57) ABSTRACT

The present disclosure relates to a novel anticancer pharmaceutical composition. The present disclosure achieves an anticancer effect using a compound effective in inhibiting the expression of ANO1 (TMEM16A). In addition, the present disclosure provides an ANO1 (TMEM16A) antagonist using the compound inhibiting the expression of ANO1 (TMEM16A).

3 Claims, 9 Drawing Sheets

PHARMACEUTICAL COMPOSITION FOR ANO1 ANTAGONIST WITH ANTICANCER ACTIVITY

CROSS-REFERENCE TO RELATED APPLICATIONS

This application claims, under 35 U.S.C. § 119, the priority of Korean Patent Application No. 10-2018-0112056 filed on Sep. 19, 2018 in the Korean Intellectual Property Office, the disclosure of which is incorporated herein by reference in its entirety.

TECHNICAL FIELD

The present disclosure relates to an anticancer pharmaceutical composition and an ANO1 antagonist.

BACKGROUND

ANO1 is a calcium-activated chloride channel (CaCC) expressed in various cells and tissues. It performs physiological functions such as the secretion of epithelial fluid, contraction of smooth muscle, cellular growth, and sensory nerve signaling.

According to recent studies, it is reported that an ANO1 inhibitor may be useful in the treatment of ANO1-related diseases such as inflammatory airway disease, hypertension and pain (*Proc. Natl. Acad. Sci. USA* 109(2012) 16354-16359; *Nat. Neurosci.* 15(2012) 1015-1021).

Recently, it was found that ANO1 is overexpressed in various cancer cells such as breast cancer, pancreatic cancer, head and neck cancer, gastrointestinal cancer and prostate cancer. ANO1 plays an important role in cellular growth, tumorigenesis and progression of cancer, and the inhibition of ANO1 significantly decreases the proliferation and migration of breast cancer, pancreatic cancer and prostate cancer cells (*Mol. Cancer.* 16(2017) 152).

ANO1 and ANO2 function as CaCCs and have high structural similarities. ANO2 is overexpressed in olfactory sensory neurons and plays an important role in olfactory signal transduction (*J. Gen. Physiol.* 148(2016) 293-311). In addition, it was found that ANO2 is involved in reduced spike generation in the thalamic cortex and hippocampal neurons and that motor dysfunction and motor learning disorder are induced in ANO2-knockout mice (*Cerebellum.* 16(2017) 929-937).

Accordingly, development of an inhibitor that selectively inhibits ANO1 over ANO2 may provide a more appropriate therapy for ANO1-related diseases than existing ANO1 inhibitors.

The ANO1 inhibitors identified until now are $CaCC_{inh}$-A01, $T16A_{inh}$-A01, MONNA, Ani9, AACT (10bm), etc. Among them, Ani9 is the most specific ANO1 inhibitor which does not inhibit ANO2.

However, there is a need for novel compounds with an increased inhibitory effect for ANO1 without inhibiting ANO2.

REFERENCES OF THE RELATED ART

Patent Documents

Korean Patent Publication No. 10-2014-0112489.
Korean Patent Registration No. 1719541.

SUMMARY

The present disclosure is directed to providing an anticancer pharmaceutical composition, which contains a novel compound effective in inhibiting the expression of ANO1 (TMEM16A) or a pharmaceutically acceptable salt thereof as an active ingredient.

The present disclosure is also directed to providing an anticancer tablet containing the pharmaceutical composition.

The present disclosure is also directed to providing an anticancer capsule containing the pharmaceutical composition.

The present disclosure is also directed to providing an anticancer syrup containing the pharmaceutical composition.

The present disclosure is also directed to providing a method for treating cancer, which may include administering the novel compound to a mammal.

The present disclosure is also directed to providing a pharmaceutical composition for preventing or treating smooth muscle contraction disorder, which contains the novel compound or a pharmaceutically acceptable salt thereof as an active ingredient.

The present disclosure is also directed to providing a method for treating smooth muscle contraction disorder, which may include administering the novel compound to a mammal.

The present disclosure is also directed to providing a pharmaceutical composition for preventing or treating pain, which contains the novel compound or a pharmaceutically acceptable salt thereof as an active ingredient.

The present disclosure is also directed to providing a method for treating pain, which may include administering the novel compound to a mammal.

The present disclosure is also directed to providing an ANO1 (TMEM16A) antagonist containing the novel compound.

The present disclosure is also directed to providing a method for inhibiting the expression of ANO1 (TMEM16A) by treating with the novel compound.

The anticancer pharmaceutical composition of the present disclosure may contain one or more compound selected from a group consisting of compounds represented by [Chemical Formula 1] through [Chemical Formula 4] or a pharmaceutically acceptable salt thereof as an active ingredient:

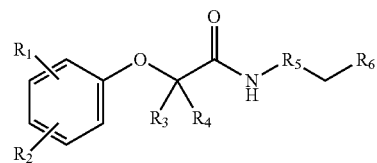

[Chemical Formula 1]

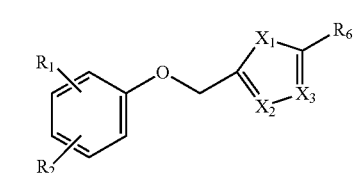

[Chemical Formula 2]

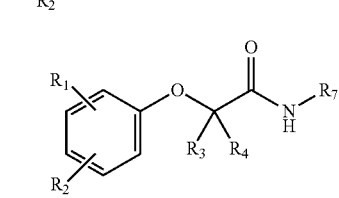

[Chemical Formula 3]

-continued

[Chemical Formula 4]

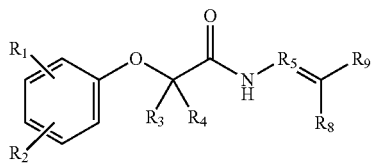

wherein
each of $R_1$ and $R_2$, which are identical to or different from each other, is independently selected from hydrogen, a halogen, $C_1$-$C_6$ alkyl and $C_1$-$C_6$ alkoxy;
each of $R_3$ and $R_4$, which are identical to or different from each other, is independently selected from hydrogen, a halogen, $C_1$-$C_6$ alkyl and $C_1$-$C_6$ alkoxy;
$R_5$ is selected from C, N, S and O;
$R_6$ is selected from

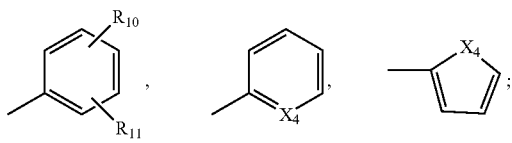

$R_7$ is selected from

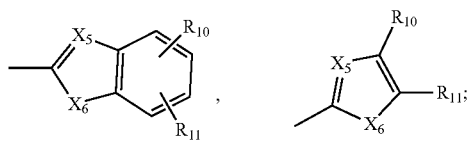

$R_8$ is selected from hydrogen, a halogen, $C_1$-$C_6$ alkyl and $C_1$-$C_6$ alkoxy;
$R_9$ is selected from

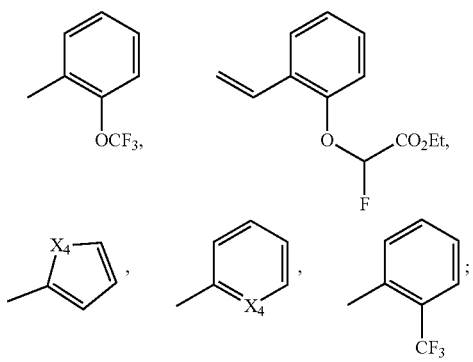

each of $R_{10}$ and $R_{11}$, which are identical to or different from each other, is independently selected from hydrogen, a halogen, $C_1$-$C_6$ alkyl, carbonyl and $C_1$-$C_6$ alkoxy;
each of $X_1$ through $X_3$, which are identical to or different from each other, is independently selected from C, N, O and S;
$X_4$ is selected from C, N, O and S; and
each of $X_5$ and $X_6$, which are identical to or different from each other, is independently selected from hydrogen, a halogen, $C_1$-$C_6$ alkyl, carbonyl and $C_1$-$C_6$ alkoxy.

The one or more compound selected from a group consisting of compounds represented by [Chemical Formula 1] through [Chemical Formula 4] may have an $IC_{50}$ [μM] for ANO1 of 0.01-65, specifically 0.01-0.08.

The one or more compound selected from a group consisting of compounds represented by [Chemical Formula 1] through [Chemical Formula 4] may inhibit the expression of ANO1 (TMEM16A) present in a cancer cell or a tumor cell.

The salt may be in one or more form selected from a group consisting of a hydrate, a solvate and a crystal.

A disease for which an anticancer effect is achieved by the pharmaceutical composition may be one or more selected from a group consisting of prostate cancer, thyroid cancer, stomach cancer, colon cancer, lung cancer, breast cancer, liver cancer, pancreatic cancer, testicular cancer, oral cancer, basal cell carcinoma, brain tumor, gallbladder cancer, cholangiocarcinoma, laryngeal cancer, retinoblastoma, cancer of the ampulla of Vater, bladder cancer, peritoneal cancer, adrenal cancer, non-small cell lung cancer, tongue cancer, small cell lung cancer, small intestine cancer, meningioma, esophageal cancer, renal pelvic/ureteral cancer, kidney cancer, malignant bone tumor, malignant soft tissue tumor, malignant lymphoma, malignant melanoma, eye neoplasm, urethral cancer, stomach cancer, sarcoma, pharynx cancer, cervical cancer, endometrial cancer, uterine sarcoma, metastatic brain tumor, colorectal cancer, vaginal cancer, spinal tumor, salivary gland cancer, tonsillar cancer, squamous cell carcinoma and anal cancer.

The anticancer tablet of the present disclosure may contain the pharmaceutical composition.

The anticancer capsule of the present disclosure may contain the pharmaceutical composition.

The anticancer syrup of the present disclosure may contain the pharmaceutical composition.

The method for treating cancer of the present disclosure may include administering the one or more compound selected from a group consisting of compounds represented by [Chemical Formula 1] through [Chemical Formula 4] to a mammal.

The pharmaceutical composition for preventing or treating smooth muscle contraction disorder of the present disclosure may contain the one or more compound selected from a group consisting of compounds represented by [Chemical Formula 1] through [Chemical Formula 4] or a pharmaceutically acceptable salt thereof as an active ingredient.

The smooth muscle contraction disorder may be one or more selected from a group consisting of inflammatory airway disease, hypertension and asthma.

The method for treating smooth muscle contraction disorder of the present disclosure may include administering the one or more compound selected from a group consisting of compounds represented by [Chemical Formula 1] through [Chemical Formula 4] to a mammal.

The pharmaceutical composition for preventing or treating pain disorder of the present disclosure may the one or more compound selected from a group consisting of compounds represented by [Chemical Formula 1] through [Chemical Formula 4] or a pharmaceutically acceptable salt thereof as an active ingredient.

The pain may be one or more selected from a group consisting of inflammatory nociceptive pain, inflammatory pain and neuropathic pain.

The method for treating pain of the present disclosure may include administering the one or more compound selected from a group consisting of compounds represented by [Chemical Formula 1] through [Chemical Formula 4] to a mammal.

The ANO1 (TMEM16A) antagonist of the present disclosure may be an ANO1 (TMEM16A) antagonist containing one or more compound selected from a group consisting of compounds represented by [Chemical Formula 1] through [Chemical Formula 4], and the antagonist may inhibit the expression of ANO1 (TMEM16A) in vitro.

The method for inhibiting the expression of ANO1 (TMEM16A) of the present disclosure may include a step of inhibiting the expression of ANO1 (TMEM16A) in vitro by treating with a substance containing one or more compound selected from a group consisting of compounds represented by [Chemical Formula 1] through [Chemical Formula 4].

The anticancer pharmaceutical composition of the present disclosure may selectively inhibit the activity of ANO1 (TMEM16A) over ANO2 most strongly. It can inhibit the proliferation of PC-3 cells in a dose-dependent manner and exhibits very superior effect of reducing the ANO1 protein as compared to the existing Ani9 as well as superior plasma stability.

The ANO1 (TMEM16A) is a kind of CaCC present in a cancer cell or a tumor, and the inhibition of the expression of ANO1 (TMEM16A) is known to have anticancer activity. Therefore, the anticancer pharmaceutical composition according to the present disclosure achieves anticancer effect by containing a compound effective in inhibiting the activity of ANO1 (TMEM16A). In addition, an ANO1 (TMEM16A) antagonist can be provided using a compound which inhibits the expression of ANO1 (TMEM16A).

DETAILED DESCRIPTION OF EMBODIMENTS

Figure 1A:
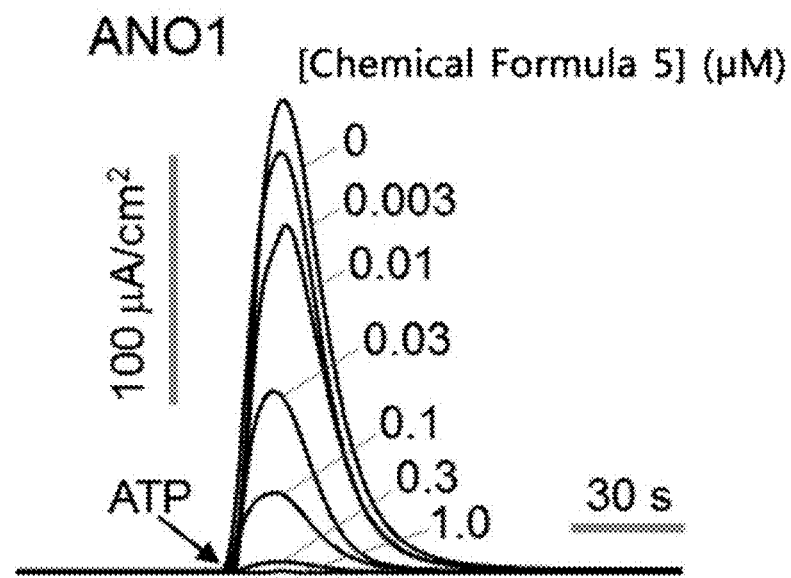
FIG. 1A shows a result of measuring the apical membrane current of FRT cells expressing ANO1.

The present disclosure relates to a novel anticancer pharmaceutical composition which is effective in inhibiting the expression of ANO1 (TMEM16A).

Hereinafter, the present disclosure is described in detail.

The novel anticancer pharmaceutical composition of the present disclosure contains one or more compound selected from a group consisting of compounds represented by [Chemical Formula 1] through [Chemical Formula 4] or a pharmaceutically acceptable salt thereof as an active ingredient:

[Chemical Formula 1]

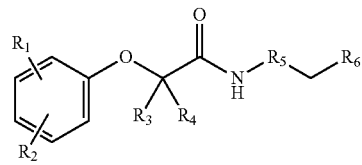

[Chemical Formula 2]

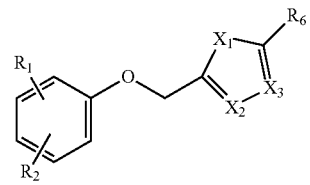

[Chemical Formula 3]

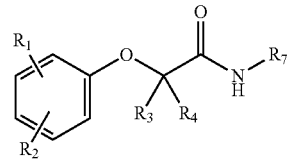

[Chemical Formula 4]

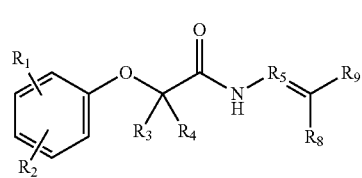

wherein
each of $R_1$ and $R_2$, which are identical to or different from each other, is independently selected from hydrogen, a halogen, $C_1$-$C_6$ alkyl and $C_1$-$C_6$ alkoxy;

each of $R_3$ and $R_4$, which are identical to or different from each other, is independently selected from hydrogen, a halogen, $C_1$-$C_6$ alkyl and $C_1$-$C_6$ alkoxy;

$R_5$ is selected from C, N, S and O;

$R_6$ is selected from

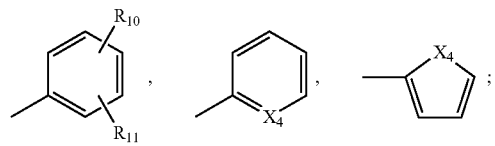

$R_7$ is selected from

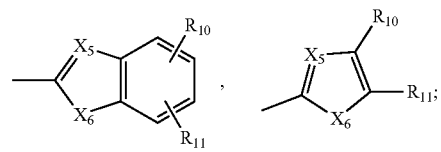

$R_8$ is selected from hydrogen, a halogen, $C_1$-$C_6$ alkyl and $C_1$-$C_6$ alkoxy;

$R_9$ is selected from

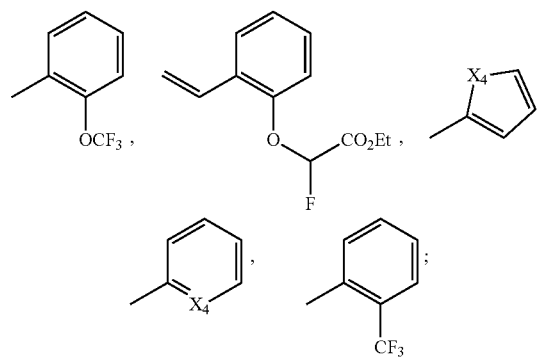

each of $R_{10}$ and $R_{11}$, which are identical to or different from each other, is independently selected from hydrogen, a halogen, $C_1$-$C_6$ alkyl, carbonyl and $C_1$-$C_6$ alkoxy;

each of $X_1$ through $X_3$, which are identical to or different from each other, is independently selected from C, N, O and S;

$X_4$ is selected from C, N, O and S; and each of $X_5$ and $X_6$, which are identical to or different from each other, is independently selected from hydrogen, a halogen, $C_1$-$C_6$ alkyl, carbonyl and $C_1$-$C_6$ alkoxy.

The $C_1$-$C_6$ alkyl may be any one selected from a group consisting of methyl, ethyl, isopropyl, propyl, butyl, isobutyl, t-butyl, pentyl and hexyl, the $C_1$-$C_6$ alkoxy may be any one selected from a group consisting of methoxy, ethoxy, isopropoxy, propoxy, butoxy, isobutoxy, t-butoxy, pentoxy and hexoxy, and the halogen may be any one selected from a group consisting of fluorine, chlorine, bromine, iodine and astatine.

Specifically, in the one or more compound selected from a group consisting of compounds represented by [Chemical Formula 1] through [Chemical Formula 4], $R_6$ may be any one selected from a group consisting of

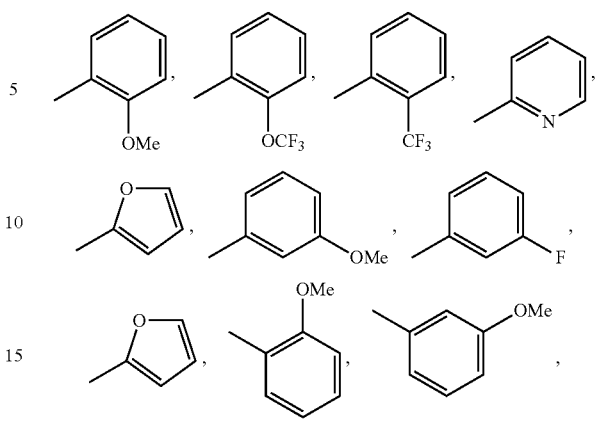

$R_7$ may be any one selected from a group consisting of

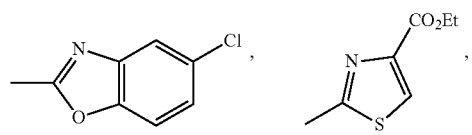

and $R_9$ may be any one selected from a group consisting of

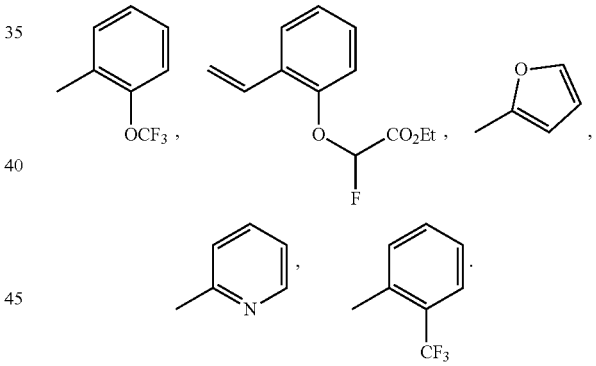

Specifically, the one or more compound selected from a group consisting of compounds represented by [Chemical Formula 1] through [Chemical Formula 4]having the above-described structure may be any one selected from a group consisting of compounds represented by [Chemical Formula 5] through [Chemical Formula 18], although not being limited thereto.

[Chemical Formula 5]

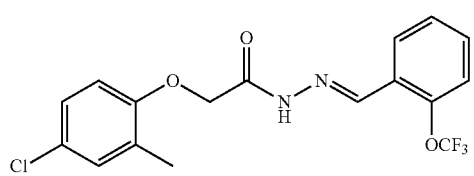

-continued

[Chemical Formula 6]
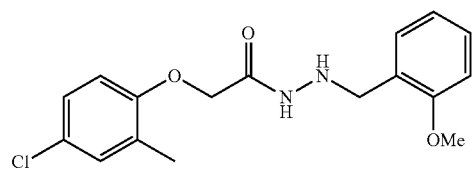

[Chemical Formula 7]
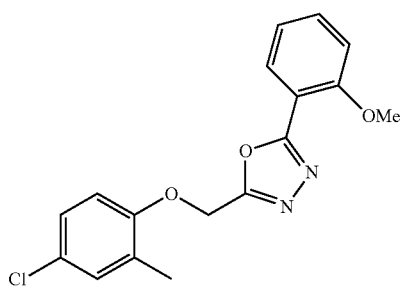

[Chemical Formula 8]

[Chemical Formula 9]
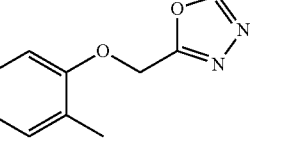

[Chemical Formula 10]
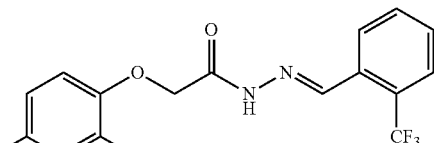

[Chemical Formula 11]
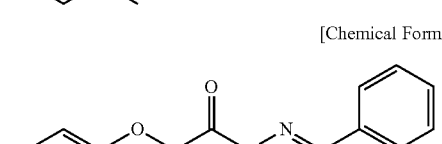

[Chemical Formula 12]
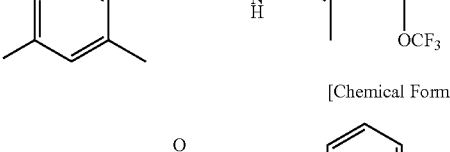

-continued

[Chemical Formula 13]
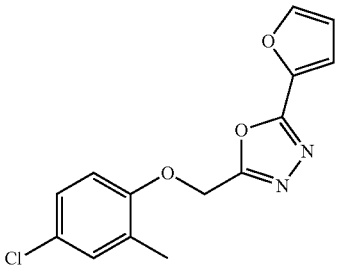

[Chemical Formula 14]
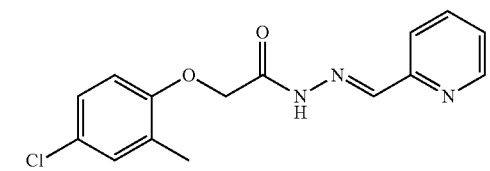

[Chemical Formula 15]
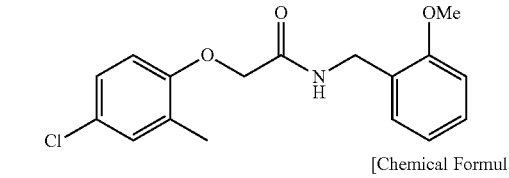

[Chemical Formula 16]
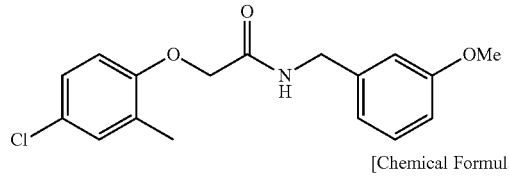

[Chemical Formula 17]
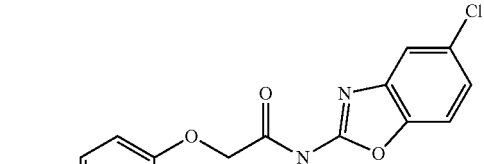

[Chemical Formula 18]
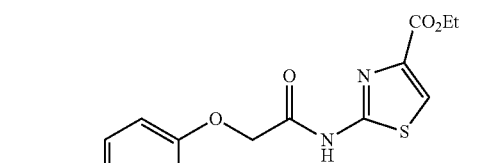

In the present disclosure, the one or more compound selected from a group consisting of compounds represented by [Chemical Formula 1] through [Chemical Formula 4] has an $IC_{50}$ [μM] of 0.01-65, specifically 0.01-0.08.

Specifically, the pharmaceutical composition may contain a pharmaceutically acceptable salt of the one or more compound selected from a group consisting of compounds represented by [Chemical Formula 1] through [Chemical Formula 4], although not being specially limited thereto. For example, the pharmaceutically acceptable salt may be any one if the solubility of the one or more compound selected from a group consisting of compounds represented by

[Chemical Formula 1] through [Chemical Formula 4] can be increased. In a specific exemplary embodiment, it may be an acid addition salt.

The pharmaceutically acceptable salt should be less toxic to the human body and should not negatively affect the biological activity and physicochemical properties of the parent compound. A free acid that may be used to prepare the pharmaceutically acceptable salt may be classified into an inorganic acid and an organic acid. As the inorganic acid, hydrochloric acid, sulfuric acid, nitric acid, phosphoric acid, perchloric acid, bromic acid, etc. may be used. As the organic acid, acetic acid, methanesulfonic acid, ethanesulfonic acid, p-toluenesulfonic acid, fumaric acid, maleic acid, malonic acid, phthalic acid, succinic acid, lactic acid, citric acid, citric acid, gluconic acid, tartaric acid, salicylic acid, malic acid, oxalic acid, benzoic acid, embonic acid, aspartic acid, glutamic acid, etc. may be used. An organic base that may be used to prepare an organic base addition salt includes tris(hydroxymethyl)methylamine, dicylcohexylamine, etc. An amino acid that may be used to prepare an amino acid addition salt is an natural amino acid such as alanine, glycine, etc. In addition, the one or more compound selected from a group consisting of compounds represented by [Chemical Formula 1] through [Chemical Formula 4] according to the present disclosure may also include, in addition to the pharmaceutically acceptable salt, any hydrate or solvate. The hydrate or solvate may be crystallized or recrystallized after dissolving the one or more compound selected from a group consisting of compounds represented by [Chemical Formula 1] through [Chemical Formula 4] in a water-miscible solvent such as methanol, ethanol, acetone or 1,4-dioxane and then adding a free acid or a free base. In this case, a solvate (particularly, hydrate) may be formed. Therefore, in addition to various water-containing compounds that may be prepared with the one or more compound selected from a group consisting of compounds represented by [Chemical Formula 1] through [Chemical Formula 4] of the present disclosure by a method such as lyophilization, stoichiometric solvates including hydrate may be included as well.

The one or more compound selected from a group consisting of compounds represented by [Chemical Formula 1] through [Chemical Formula 4] or a pharmaceutically acceptable salt thereof may be contained in an amount of specifically 1-80 parts by weight, more specifically 20-60 parts by weight, based on 100 parts by weight of the total composition, although not being specially limited thereto. If the content of the one or more compound selected from a group consisting of compounds represented by [Chemical Formula 1] through [Chemical Formula 4] or a pharmaceutically acceptable salt thereof is less than 1 part by weight, it is difficult to sufficiently achieve the anticancer activity to be accomplished in the present disclosure. And, if the one or more compound selected from a group consisting of compounds represented by [Chemical Formula 1] through [Chemical Formula 4] or a pharmaceutically acceptable salt thereof exceeds 80 parts by weight, the contents of other substances used to prepare a pharmaceutical product may be limited disadvantageously.

Although the administration method of the anticancer pharmaceutical composition is not specially limited, it may be administered specifically intraarterially, intravenously, subcutaneously, intrarectally, intranasally, or via any other parenteral route. More specifically, it may be administered intraarterially, intravenously, orally, or directly into muscle cells.

The administration dosage of the composition will vary depending on the activity of the compound, administration route, severity of the condition to be treated, and previous medical history. However, increasing the administration dosage gradually starting from a level lower than required to achieve the desired therapeutic effect until the desired effect is achieved is within the level of the related art, and the desirable administration dosage may be determined depending on age, sex, somatotype and body weight. The composition may be processed further until it is prepared into a pharmaceutically acceptable formulation. The formulation of the composition may be determined generally although it will vary depending on pathological conditions and patients to be treated.

A disease for which an anticancer effect is achieved by the pharmaceutical composition may be any disease for which an anticancer effect is achieved by inhibiting the expression of ANO1 (TMEM16A) present in a cancer cell or a tumor cell. Specifically, an anticancer effect may be achieved for one or more disease selected from a group consisting of prostate cancer, thyroid cancer, stomach cancer, colon cancer, lung cancer, breast cancer, liver cancer, pancreatic cancer, testicular cancer, oral cancer, basal cell carcinoma, brain tumor, gallbladder cancer, cholangiocarcinoma, laryngeal cancer, retinoblastoma, cancer of the ampulla of Vater, bladder cancer, peritoneal cancer, adrenal cancer, non-small cell lung cancer, tongue cancer, small cell lung cancer, small intestine cancer, meningioma, esophageal cancer, renal pelvic/ureteral cancer, kidney cancer, malignant bone tumor, malignant soft tissue tumor, malignant lymphoma, malignant melanoma, eye neoplasm, urethral cancer, stomach cancer, sarcoma, pharynx cancer, cervical cancer, endometrial cancer, uterine sarcoma, metastatic brain tumor, colorectal cancer, vaginal cancer, spinal tumor, salivary gland cancer, tonsillar cancer, squamous cell carcinoma and anal cancer.

A method for treating cancer of the present disclosure may include administering the one or more compound selected from a group consisting of compounds represented by [Chemical Formula 1] through [Chemical Formula 4] to a mammal.

The pharmaceutical composition of the present disclosure may prevent or treat smooth muscle contraction disorder, and the smooth muscle contraction disorder may be one or more selected from a group consisting of inflammatory airway disease, hypertension and asthma.

A method for treating smooth muscle contraction disorder of the present disclosure may include administering the one or more compound selected from a group consisting of compounds represented by [Chemical Formula 1] through [Chemical Formula 4] to a mammal.

The pharmaceutical composition of the present disclosure may prevent or treat pain, and the pain may be one or more selected from a group consisting of inflammatory nociceptive pain, inflammatory pain and neuropathic pain.

A method for treating pain of the present disclosure may include administering the one or more compound selected from a group consisting of compounds represented by [Chemical Formula 1] through [Chemical Formula 4] to a mammal.

According to recent studies, it is reported that an ANO1 inhibitor may be useful in the treatment of ANO1-related diseases such as inflammatory airway disease, hypertension and pain (*Proc. Natl. Acad. Sci. USA* 109(2012) 16354-16359; *Nat. Neurosci.* 15(2012) 1015-1021).

The ANO1 inhibitor may provide an advantageous effect for inflammatory airway disease by inhibiting mucus hypersecretion from the airway epithelium and inhibiting the contraction of smooth muscle (*Proc. Natl. Acad. Sci. U.S.A.* 109(2012) 16354-16359), and remarkably decreases the blood pressure of hypertensive mouse (*Am. J. Physiol.* 303(2012) C1229-C1243; *J. Mol. Cell. Cardiol.* 82(2015) 22-32). In addition, the inhibition of ANO1 activity in a mouse thermal pain model significantly reduces the pain of mouse and also reduces capsaicin-induced pain-related behavior (*Proc. Natl. Acad. Sci. U.S.A.* 112(2015) 5213-5218; *Mol. Pain* 11 (2015 Sep. 12) 55).

Meanwhile, the pharmaceutical composition according to the present disclosure may be used as being added to a tablet, a capsule or a syrup.

A method for preparing the tablet is not particularly limited. In a specific exemplary embodiment, it is prepared by sieving a pharmaceutical composition containing the one or more compound selected from a group consisting of compounds represented by [Chemical Formula 1] through [Chemical Formula 4] or a pharmaceutically acceptable salt thereof, mixing with lactose, starch and pregelatinized corn starch, granulating the resulting powder by adding purified water, drying the resulting granule, mixing with magnesium stearate, and compressing the resulting mixture. Preferred ingredients of the tablet and their contents are 5.0 mg of the pharmaceutical composition according to the present disclosure, 150.0 mg of lactose BP, 30.0 mg of starch BP, 15.0 mg of pregelatinized corn starch BP and 1.0 mg of magnesium stearate.

A method for preparing the capsule is not particularly limited. In a specific exemplary embodiment, it is prepared by sieving a pharmaceutical composition containing the one or more compound selected from a group consisting of compounds represented by [Chemical Formula 1] through [Chemical Formula 4] or a pharmaceutically acceptable salt thereof, mixing with an excipient, and filling the resulting mixture in a gelatin capsule. Preferred ingredients of the capsule and their contents are 5.0 mg of the pharmaceutical composition according to the present disclosure, 100.0 mg of starch and 1.0 mg of magnesium stearate BP.

A method for preparing the syrup is not particularly limited. In a specific exemplary embodiment, it is prepared by dissolving white sugar in 500 mL of purified water, dissolving sodium carboxymethyl cellulose in 400 mL of purified water in a separate container, mixing the white sugar dissolved in purified water with the sodium carboxymethyl cellulose dissolved in purified water, adding and dissolving methylparaben and propylparaben, adding ethanol and then adding purified water to make the total volume of the solution 1,000 mL, and then suspending a pharmaceutical composition containing the one or more compound selected from a group consisting of compounds represented by [Chemical Formula 1] through [Chemical Formula 4] or a pharmaceutically acceptable salt thereof therein. Preferred ingredients of the capsule and their contents are 5.0 g of the pharmaceutical composition according to the present disclosure, 637.5 g of white sugar, 2.0 g of sodium carboxymethyl cellulose, 0.28 g of methylparaben, 0.12 g of propylparaben, 20 mL of ethanol and purified water as balance.

The present disclosure also provides an ANO1 (TMEM16A) antagonist.

The ANO1 (TMEM16A) antagonist of the present disclosure contains the one or more compound selected from a group consisting of compounds represented by [Chemical Formula 1] through [Chemical Formula 4].

The antagonist is an ANO1 (TMEM16A) antagonist which inhibits the activity of ANO1 (TMEM16A) in vitro.

By containing the one or more compound selected from a group consisting of compounds represented by [Chemical Formula 1] through [Chemical Formula 4], the ANO1 (TMEM16A) antagonist according to the present disclosure inhibits or decreases the activity of ANO1 (TMEM16A). As a result, the ANO1 (TMEM16A) antagonist according to the present disclosure inhibits or decreases the expression of ANO1 (TMEM16A) and may achieve an anticancer effect when applied into the body (in vivo). The inventors of the present disclosure have noticed the effect of the one or more compound selected from a group consisting of compounds represented by [Chemical Formula 1] through [Chemical Formula 4] of inhibiting the activity of ANO1 (TMEM16A), and claim the ANO1 (TMEM16A) antagonist according to the present disclosure in order to seek protection for the effect of inhibiting the activity of ANO1 (TMEM16A) in vitro under Article 2(1) of the Korean Patent Act, in addition to the medicinal invention.

The inhibition or decrease of the expression of ANO1 (TMEM16A) is achieved by the one or more compound selected from a group consisting of compounds represented by [Chemical Formula 1] through [Chemical Formula 4].

The present disclosure also provides a method for inhibiting the expression of ANO1 (TMEM16A).

The method for inhibiting the expression of ANO1 (TMEM16A) of the present disclosure includes a step of inhibiting the expression of ANO1 (TMEM16A) in vitro by treating with a substance containing the one or more compound selected from a group consisting of compounds represented by [Chemical Formula 1] through [Chemical Formula 4].

Hereinafter, specific examples will be provided to help understanding of the present disclosure. However, the following examples are for provided only as examples for illustrating the present disclosure and it will be apparent to those skilled in the art that various changes and modifications can be made within the spirit and scope of the disclosure and such changes and modifications belong to the scope of the appended claims.

EXAMPLES

Synthesis Example 1. Compound Represented by [Chemical Formula 5]

[Chemical Formula 5]

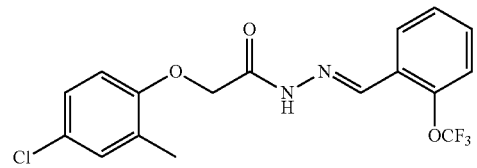

2-(4-Chloro-2-methylphenoxy)acetohydrazide (100 mg, 0.47 mmol) and 2-(trifluoromethoxy)benzaldehyde (79 μL, 1.2 eq.) were added to EtOH (2.5 mL) and the resulting mixture was stirred at 80° C. for 16 hours. The precipitated product was filtered, collected and dried, affording a white solid represented by [Chemical Formula 5].

White solid, mp: 157.2-158.0° C.; $^1$H NMR (400 MHz, DMSO-$d_6$) δ 11.83 (s, 1H, isomer b), 11.76 (s, 1H, isomer a), 8.57 (s, 1H, isomer b), 8.27 (s, 1H, isomer a), 8.06 (d, J=7.6 Hz, 1H, isomer a), 8.02 (d, J=8.0 Hz, 1H, isomer b), 7.62-6.54 (m, 3H, isomer b), 7.52-7.43 (m, 3H, isomer a), 7.28-7.12 (m, 3H, isomer a), 6.92-6.84 (m, 3H, isomer b), 5.2 (s, 2H, isomer a), 4.71 (s, 2H, isomer b), 2.24 (s, 3H, isomer b), 2.21 (s, 3H, isomer a); $^{13}$C NMR (100 MHz, DMSO-d$_6$) δ 169.0, 155.2, 140.8, 137.2, 131.6, 130.1, 129.9, 128.4, 128.1, 128.0, 127.0, 126.9, 126.6, 126.4, 126.2, 124.0, 121.8, 113.1, 67.0, 65.3, 15.9; HRMS (ESI-QTOF) m/z [M+H]$^+$ calcd for C$_{17}$H$_{15}$ClF$_3$N$_2$O$_3$ 387.0718, found 387.0719.

Synthesis Example 2. Compound Represented by [Chemical Formula 6]

[Chemical Formula 6]

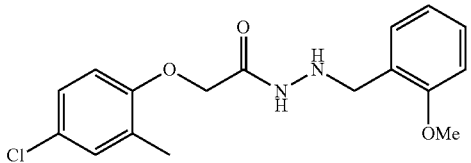

After adding Et$_3$SiH (19.2 µL, 2 eq.) to a solution of Ani9 (20 mg, 0.06 mmol, Korean Patent Registration No. 1719541) in TFA (1 mL) at 0° C. and stirring for 1 hour at the same temperature, the reaction mixture was diluted with 15% aq. HCl (1 mL) and washed with hexane (1 mL). Then, the aqueous layer was cautiously basified with KOH pellets and extracted with CH$_2$Cl$_2$ (1 mL×2). The organic layer was dried with MgSO$_4$ and concentrated under reduced pressure. The obtained crude residue was purified by silica gel column chromatography (hexane:ethyl acetate:dichloromethane=10:1:2, volume ratio), affording a [Chemical Formula 6] compound as a white solid.

White solid, mp: 98.2-100.6° C.; $^1$H NMR (400 MHz, CDCl$_3$) δ 7.73 (br s, 1H), 7.29 (t, J=7.0 Hz, 1H), 7.18 (dd, J=1.2, 7.6 Hz, 1H), 7.14-7.09 (m, 2H), 6.93-6.87 (m, 2H), 6.56 (d, J=8.4 Hz, 1H), 5.04 (s, 1H), 4.50 (s, 2H), 4.04 (s, 2H), 3.86 (s, 3H), 2.11 (s, 3H); $^{13}$C NMR (100 MHz, CDCl$_3$) δ 166.8, 158.1, 154.0, 131.0, 130.9, 129.5, 128.5, 126.9, 126.8, 125.1, 120.6, 112.5, 110.6, 67.5, 55.6, 51.7, 16.3; HRMS (ESI-QTOF) m/z [M+H]$^+$ calcd for C$_{17}$H$_{20}$ClN$_2$O$_3$ 335.1157, found 335.1154.

Synthesis Example 3. Compound Represented by [Chemical Formula 7]

[Chemical Formula 7]

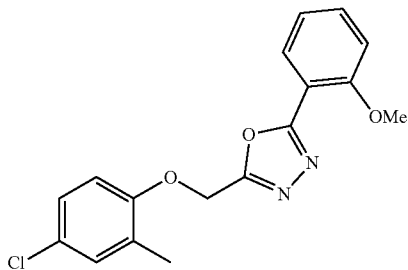

After adding iodobenzene diacetate (32 mg, 1.1 eq.) to a solution of Ani9 (30 mg, 0.090 mmol, Korean Patent Registration No. 1719541) in CH$_2$Cl$_2$ (1 mL) at room temperature and stirring at room temperature for 6 hours, the reaction mixture was concentrated under vacuum. The obtained crude residue was purified by silica gel column chromatography (hexane:ethyl acetate:dichloroethane=20: 1:2 to 10:1:2, volume ratio), affording a [Chemical Formula 7] compound as a white solid.

White solid, mp: 104.8-105.9° C.; $^1$H NMR (400 MHz, CDCl$_3$) δ 7.93 (d, J=8.0 Hz, 1H), 7.52 (t, J=8.0 Hz, 1H), 7.16-7.04 (m, 4H), 6.95 (d, J=8.8 Hz, 1H), 5.231 (s, 2H), 3.95 (s, 3H), 2.23 (s, 3H); $^{13}$C NMR (100 MHz, CDCl$_3$) δ 164.7, 162.0, 158.1, 154.6, 133.6, 131.0, 129.5, 126.8, 126.7, 120.9, 113.2, 112.7, 112.1, 60.7, 56.1, 16.3; HRMS (ESI-QTOF) m/z [M+Na]$^+$ calcd for C$_{17}$H$_{15}$ClN$_2$NaO$_3$ 355.0820, found 355.0822.

Synthesis Example 4. Compound Represented by [Chemical Formula 8]

[Chemical Formula 8]

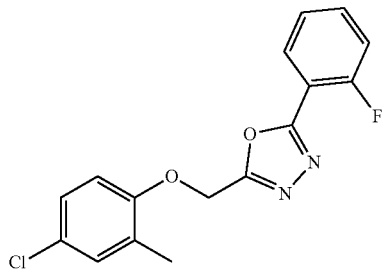

After adding iodobenzene diacetate (33 mg, 1.1 eq.) to a solution of

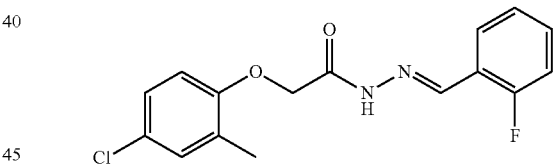

(30 mg, 0.094 mmol) in CH$_2$Cl$_2$ (1 mL) at room temperature and stirring at room temperature for 16 hours, the reaction mixture was concentrated under vacuum. The obtained crude residue was purified by silica gel column chromatography (hexane:ethyl acetate:dichloroethane=20:1:2, volume ratio), affording a [Chemical Formula 8] compound as a white solid.

White solid, mp: 96.8-98.7° C.; $^1$H NMR (400 MHz, CDCl$_3$) δ 8.08 (t, J=7.6 Hz, 1H), 7.60-7.53 (m, 1H), 7.31 (t, J=7.6 Hz, 1H), 7.26 (t, J=9.2 Hz, 1H), 7.16-7.11 (m, 2H), 6.94 (d, J=9.2 Hz, 1H), 5.34 (s, 2H), 2.24 (s, 3H); $^{13}$C NMR (100 MHz, CDCl$_3$) δ 162.7, 161.5, 158.9, 154.5, 134.1, 134.0, 131.1, 130.0, 129.99, 129.6, 127.0, 126.7, 124.9, 124.86, 117.3, 117.1, 113.1, 60.5, 16.2; HRMS (ESI-QTOF) m/z [M+H]$^+$ calcd for C$_{16}$H$_{13}$ClFN$_2$O$_2$ 319.0644, found 319.0641.

Synthesis Example 5. Compound Represented by [Chemical Formula 9][Chemical Formula 9]

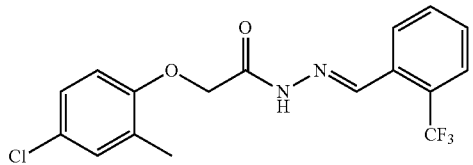

After stirring a mixture of 2-(4-chloro-2-methylphenoxy) acetohydrazide (100 mg, 0.47 mmol) and 2-(trifluoromethyl)benzaldehyde (74 μL, 1.2 eq.) in EtOH (2.5 mL) at 80° C. for 12 hours, the precipitated product was filtered, collected and dried, affording a [Chemical Formula 9] compound as a white solid.

White solid, mp: 158.2-160.0° C.; $^1$H NMR (400 MHz, DMSO-d$_6$) δ 11.95 (s, 1H, isomer b), 11.87 (s, 1H, isomer a), 8.66 (s, 1H, isomer b), 8.36 (s, 1H, isomer a), 8.22 (d, J=8 Hz, 1H, isomer a), 8.17 (d, J=8 Hz, 1H, isomer b), 7.83-7.7 (m, 3H, isomer a), 7.67-7.58 (m, 3H, isomer b), 7.27-7.12 (m, 3H, isomer a), 6.93-6.86 (m, 3H, isomer b), 5.23 (s, 2H, isomer a), 4.72 (s, 2H, isomer b), 2.24 (s, 3H, isomer b), 2.21 (s, 3H, isomer a); $^{13}$C NMR (100 MHz, DMSO-d$_6$) δ 169.2, 164.6, 155.2, 155.0, 139.0, 132.8, 131.8, 130.1, 130.0, 129.9, 128.4, 127.1, 126.9, 126.4, 126.2, 125.9, 124.0, 113.3, 113.1, 67.0, 65.3, 15.9; HRMS (ESI-QTOF) m/z [M+H]$^+$ calcd for C$_{17}$H$_{15}$ClF$_3$N$_2$O$_2$ 371.0769, found 371.0765.

Synthesis Example 6. Compound Represented by [Chemical Formula 10]

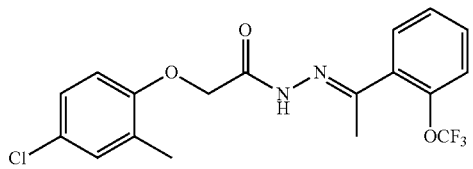

After stirring a mixture of 2-(4-chloro-2-methylphenoxy) acetohydrazide (100 mg, 0.47 mmol) and 1-(2-(trifluoromethoxy)phenyl)ethan-1-one (45 μL, 1.2 eq.) in EtOH (2.5 mL) at 80° C. for 12 hours, the precipitated product was filtered, collected and dried for 5 hours, affording a [Chemical Formula 10] compound as a white solid.

White solid, mp: 119.2-121.0° C.; $^1$H NMR (400 MHz, CDCl$_3$) δ 9.56 (s, 1H, isomer a), 9.35 (s, 1H, isomer b), 7.67 (d, J=7.6 Hz, 1H, isomer a), 7.48 (d, J=7.6 Hz, 1H, isomer b), 7.52-7.4 (m, 3H, isomer b), 7.37-7.28 (m, 3H, isomer a), 7.23-7.15 (m, 2H, isomer a), 7.12 (s, 1H, isomer b), 7.05 (dd, J=2.0, 8.6 Hz, 1H, isomer b), 5.09 (s, 2H, isomer b), 4.69 (s, 2H, isomer a), 2.34 (s, 3H, isomer a), 2.32-2.26 (m, 3H, isomer a, b), 2.21 (s, 3H, isomer b); $^{13}$C NMR (100 MHz, CDCl$_3$) δ 170.4, 163.7, 155.1, 153.5, 152.4, 147.8, 146.9, 146.7, 131.0, 130.8, 130.8, 130.6, 130.5, 130.0, 127.1, 127.0, 127.96, 126.2, 1120.5, 112.6, 112.4, 67.4, 66.1, 16.4, 16.3, 16.2, 16.16; HRMS (ESI-QTOF) m/z [M+H]$^+$ calcd for C$_{18}$H$_{17}$ClFN$_2$O$_3$ 401.0874, found 401.0873.

Synthesis Example 7. Compound Represented by [Chemical Formula 11]

[Chemical Formula 11]

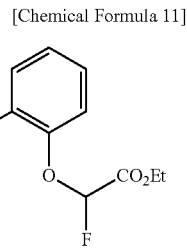

After stirring a mixture of 2-(4-chloro-2-methylphenoxy) acetohydrazide (100 mg, 0.47 mmol), ethyl 2-fluoro-2-(2-formylphenoxy)acetate (126 mg, 1.2 eq.) and AcOH (0.25 mL, solvent, 10 vol %) at 80° C. for 12 hours, the precipitated product was filtered, collected and dried, affording a [Chemical Formula 11] compound as a white solid.

The ethyl 2-fluoro-2-(2-formylphenoxy)acetate was obtained as follows. After adding K$_2$CO$_3$ (679 mg, 3 eq.) to a mixture of 2-hydroxybenzaldehyde (200 mg, 1.64 mmol) and ethyl 2-bromo-2-fluoroacetate (230 μL, 1.2 eq.) in acetone (6 mL) and stirring at room temperature for 3 hours, the reaction mixture was concentrated under vacuum. The obtained crude residue was extracted with an organic mixture of CH$_2$Cl$_2$ and H$_2$O. After drying the organic layer on MgSO$_4$ and concentrating under vacuum, the residue was purified by silica gel column chromatography (hexane:ethyl acetate:dichloroethane=20:1:2, volume ratio), affording ethyl 2-fluoro-2-(2-formylphenoxy)acetate as a colorless oil.

White solid, mp: 100.3-101.5° C.; $^1$H NMR (400 MHz, CDCl$_3$) δ 9.50 (s, 1H, isomer a), 9.03 (s, 1H, isomer b), 8.51 (s, 1H, isomer a), 8.20-8.15 (m, 1H, isomer a, b), 7.91 (d, J=7.2 Hz, isomer b), 7.47-7.40 (m, 1H, isomer a, b), 7.25-7.12 (m, 4H for isomer a, 3H for isomer b), 7.07 (dd, J=8.4 Hz, 1H, isomer b), 6.77 (d, J=8.4 Hz, 1H, isomer a), 6.71 (d, J=8.8 Hz, 1H, isomer b), 6.05-5.86 (m, 1H, isomer a, b), 5.13 (s, 2H, isomer b), 4.66 (s, 2H, isomer a), 4.41-4.32 (m, 2H, isomer a, b), 2.33 (s, 3H, isomer a), 2.30 (s, 3H, isomer b), 1.40-1.32 (m, 3H, isomer a, b); $^{13}$C NMR (100 MHz, CDCl$_3$) δ 169.4, 164.1, 163.8, 155.1, 154.4, 153.9, 144.0, 139.5, 132.3, 132.0, 131.0, 130.7, 127.6, 127.0, 126.2, 125.0, 116.9, 116.7, 113.1, 112.7, 103.9, 103.8, 101.6, 101.56, 67.8, 66.2, 62.9, 62.8, 16.3, 16.2, 14.0, 13.99; HRMS (ESI-QTOF) m/z [M+Na]$^+$ calcd for C$_{20}$H$_{20}$ClFN$_2$NaO$_5$ 445.0937, found 445.0936.

Synthesis Example 8. Compound Represented by [Chemical Formula 12]

[Chemical Formula 12]

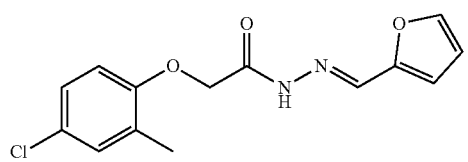

After stirring a mixture of 2-(4-chloro-2-methylphenoxy) acetohydrazide (100 mg, 0.47 mmol) and furan-2-carbaldehyde (46 μL, 1.2 eq.) in EtOH (2.5 mL) at 80° C. for 18 hours, the precipitated product was filtered, collected and dried, affording a [Chemical Formula 12] compound as a white solid.

White solid, mp: 140.5-143.7° C.; $^1$H NMR (400 MHz, DMSO-d$_6$) δ 11.57 (s, 1H, isomer a), 11.48 (s, 1H, isomer b), 8.18 (s, 1H, isomer b), 7.89 (s, 1H, isomer a), 7.86-7.81 (m, 1H, isomer a, b), 7.27-7.11 (m, 2H, isomer a, b), 6.93-6.90 (m, 1H, isomer a, b), 6.88 (d, J=8.8 Hz, 1H, isomer b), 6.8 (d, J=8.8 Hz, 1H, isomer a), 6.65-6.61 (m, 1H, isomer a, b), 5.09 (s, 2H, isomer a), 4.67 (s, 2H, isomer b), 2.23 (s, 3H, isomer b), 2.20 (s, 3H, isomer a); $^{13}$C NMR (100 MHz, DMSO-d$_6$) δ 168.6, 164.1, 155.2, 154.9, 149.1, 149.0, 145.4, 145.1, 137.7, 134.0, 130.1, 129.9, 128.8, 128.4, 126.4, 126.3, 124.6, 124.0, 114.0, 113.8, 113.2, 113.0, 112.2, 112.19, 67.0, 65.0, 15.9; HRMS (ESI-QTOF) m/z [M+H]$^+$ calcd for C$_{14}$H$_{14}$ClN$_2$O$_3$ 293.0687, found 293.0687.

Synthesis Example 9. Compound Represented by [Chemical Formula 13]

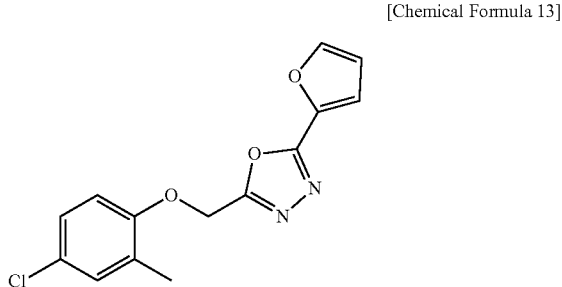 [SMILES: Cc1cc(Cl)ccc1OCc1nnc(-c2ccco2)o1]

[Chemical Formula 13]

After adding iodobenzene diacetate (36 mg, 1.1 eq.) to a solution of the [Chemical Formula 12] compound (30 mg, 0.102 mmol) in CH$_2$Cl$_2$ (1 mL) at room temperature and then stirring at room temperature for 16 hours, the reaction mixture was concentrated under vacuum. The obtained crude residue was purified by silica gel column chromatography (hexane:ethyl acetate:dichloroethane=20:1:2, volume ratio), affording a [Chemical Formula 13] compound as a white solid.

White solid, mp: 110.6-112.3° C.; $^1$H NMR (400 MHz, CDCl$_3$) δ 7.66 (s, 1H), 7.21 (d, J=3.6 Hz, 1H), 7.16-7.10 (m, 2H), 6.92 (d, J=8.0 Hz, 1H), 6.62 (dd, J=3.2 Hz, 1H), 5.30 (s, 2H), 2.23 (s, 3H); $^{13}$C NMR (100 MHz, CDCl$_3$) δ 161.6, 158.7, 154.4, 146.2, 139.1, 131.1, 129.5, 127.0, 126.7, 115.0, 113.0, 112.4, 60.3, 16.2; HRMS (ESI-QTOF) m/z [M+H]$^+$ calcd for C$_{14}$H$_{12}$ClN$_3$O$_2$ 291.0531, found 291.0530.

Synthesis Example 10. Compound Represented by [Chemical Formula 14]

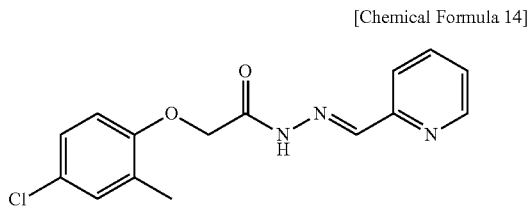 [SMILES: Cc1cc(Cl)ccc1OCC(=O)N/N=C/c1ccccn1]

[Chemical Formula 14]

After stirring a mixture of 2-(4-chloro-2-methylphenoxy) acetohydrazide (100 mg, 0.47 mmol) and picolinaldehyde (53 μL, 1.2 eq.) in EtOH (2.5 mL) at 80° C. for 12 hours, the precipitated product was filtered, collected and dried, affording a [Chemical Formula 14] compound as a white solid.

White solid, mp: 179.8-180.2° C.; $^1$H NMR (400 MHz, DMSO-de) δ 11.81 (s, 1H, isomer a, b), 8.61 (s, 1H, isomer a, b), 8.31 (s, 1H, isomer b), 8.04 (s, 1H, isomer a), 8.02-7.80 (m, 2H, isomer a, b), 7.41 (s, 1H, isomer a, b), 7.28-7.10 (m, 2H, isomer a, b), 6.95-6.64 (m, 1H, isomer a, b), 5.21 (s, 2H), 4.72 (s, 2H), 2.29-2.15 (m, 3H, isomer a, b); $^{13}$C NMR (100 MHz, DMSO-d$_6$) δ 169.1, 164.5, 155.2, 154.9, 152.8, 149.6, 149.5, 148.0, 144.3, 136.9, 136.8, 130.1, 129.9, 128.8, 128.4, 126.4, 126.3, 124.6, 124.4, 124.0, 120.0, 119.8, 113.3, 113.1, 66.9, 65.2, 15.9; HRMS (ESI-QTOF) m/z [M+H]$^+$ calcd for C$_{15}$H$_{15}$ClN$_3$O$_2$ 304.0847, found 304.0843.

Synthesis Example 11. Compound Represented by [Chemical Formula 15]

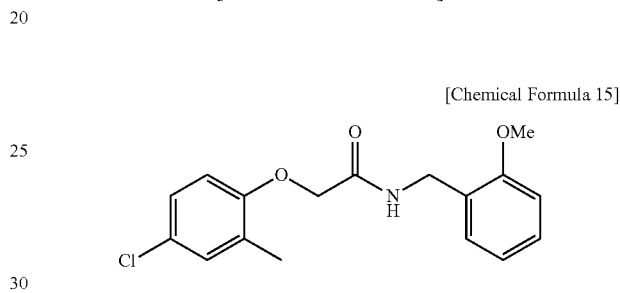

[Chemical Formula 15]

After adding 2-methoxybenzylamine (42 μL, 1.2 eq.), EDC-HCl (78 mg, 1.5 eq.), DMAP (2 mg, 0.05 eq.) and Et$_3$N (76 μL, 2 eq.) to a solution of 2-(4-chloro-2-methylphenoxy)acetic acid (53 mg, 0.26 mmol) in CH$_2$Cl$_2$ (1 mL) at 0° C. and stirring at 40° C. for 16 hours, the reaction mixture was diluted with CH$_2$Cl$_2$ (2 mL) and washed with 15% HCl (1 mL). The aqueous layer was extracted once more with CH$_2$Cl$_2$ (2 mL) and the organic layer was dried with MgSO$_4$ and concentrated under reduced pressure. The obtained crude residue was purified by silica gel column chromatography (hexane:ethyl acetate:dichloroethane=20:1:2 to 10:1:2, volume ratio), affording a [Chemical Formula 15] compound.

White solid, mp: 91.6-93.5° C.; $^1$H NMR (400 MHz, CDCl$_3$) δ 7.31-7.24 (m, 2H), 7.20 (br s, 1H), 7.13 (s, 1H), 7.08 (d, J=8.4 Hz, 1H), 6.93 (t, J=7.4 Hz, 1H), 6.87 (d, J=8.4 Hz, 1H), 6.93 (d, J=8.8 Hz, 1H), 4.53 (d, J=6.0 Hz, 2H), 4.53 (s, 2H), 3.81 (s, 3H), 2.24 (s, 3H); $^{13}$C NMR (100 MHz, CDCl$_3$) δ 167.6, 157.7, 130.8, 129.8, 129.2, 128.2, 126.9, 126.5, 125.8, 120.9, 112.5, 110.3, 67.7, 55.3, 39.4, 16.2; HRMS (ESI-QTOF) m/z [M+H]$^+$ calcd for C$_{17}$H$_{15}$ClNO$_3$ 320.1048, found 320.1045.

Synthesis Example 12. Compound Represented by [Chemical Formula 16]

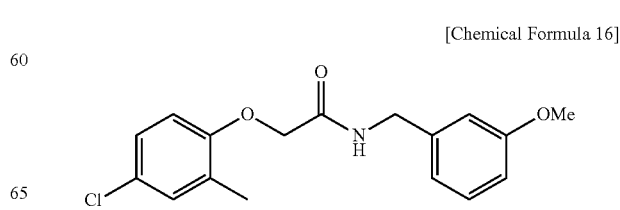

[Chemical Formula 16]

After adding 3-methoxybenzylamine (38 μL, 1.2 eq.), EDC-HCl (72 mg, 1.5 eq.), DMAP (1.5 mg, 0.05 eq.) and Et₃N (70 μL, 2 eq.) to a solution of 2-(4-chloro-2-methylphenoxy)acetic acid (50 mg, 0.25 mmol) in CH₂C₂(1 mL) at 0° C. and stirring at 40° C. for 16 hours, the reaction mixture was diluted with CH₂C₂(2 mL) and washed with 15% HCl (1 mL). The aqueous layer was extracted once more with CH₂Cl₂ (2 mL) and the organic layer was dried with MgSO₄ and concentrated under reduced pressure. The obtained crude residue was purified by silica gel column chromatography (hexane:ethyl acetate:dichloroethane=20: 1:2 to 10:1:2, volume ratio), affording a [Chemical Formula 16] compound as a white solid.

White solid, mp: 95.8-96.5° C.; ¹H NMR (400 MHz, CDCl₃) δ 7.26 (t, J=7.8 Hz, 1H), 7.16-7.10 (m, 2H), 6.88-6.78 (m, 4H), 6.70 (d, J=8.4 Hz, 1H), 4.55-4.51 (m, 4H), 3.78 (s, 3H), 2.20 (s, 3H); ¹³C NMR (100 MHz, CDCl₃) δ 168.1, 160.1, 154.1, 139.3, 131.0, 130.0, 128.5, 126.9, 119.8, 113.2, 113.2, 112.8, 68.0, 55.4, 43.1, 16.4; HRMS (ESI-QTOF) m/z [M+H]⁺ calcd for C₁₇H₁₇ClNO₃ 320.1048, found 320.1043.

Synthesis Example 13. Compound Represented by [Chemical Formula 17]

[Chemical Formula 17]

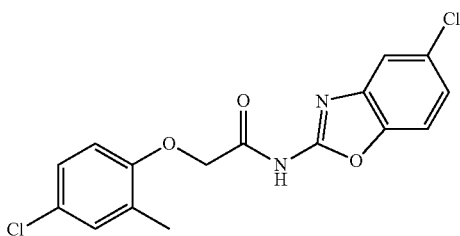

After adding 5-chlorobenzo[d]oxazol-2-amine (50 mg, 1.2 eq.), EDC-HCl (72 mg, 1.5 eq.), DMAP (1.5 mg, 0.05 eq.) and Et₃N (70 μL, 2 eq.) to a solution of 2-(4-chloro-2-methylphenoxy)acetic acid (50 mg, 0.25 mmol) in CH₂Cl₂ (1 mL) at 0° C. and stirring the mixture at 30° C. for 16 hours, the reaction mixture was diluted with CH₂Cl₂ (2 mL) and washed with 15% HCl (1 mL). The aqueous layer was extracted once more with CH₂Cl₂ (2 mL) and the organic layer was dried with MgSO₄ and concentrated under reduced pressure. The obtained crude residue was purified by silica gel column chromatography (hexane:ethyl acetate:dichloroethane=20:1:2, volume ratio), affording a [Chemical Formula 17] compound as a white solid.

White solid, mp: 165.5-168.2° C.; ¹H NMR (400 MHz, CDCl₃) δ 9.28 (br s, 1H), 7.61 (s, 1H), 7.42 (d, J=8.4 Hz, 1H), 7.27 (dd, J=2.0, 8.4 Hz, 1H), 7.20 (s, 1H), 7.16 (dd, J=2.0, 8.4 Hz, 1H), 6.75 (d, J=8.8 Hz, 1H), 4.75 (s, 2H), 2.34 (s, 3H); ¹³C NMR (100 MHz, CDCl₃) δ 165.2, 154.5, 153.5, 146.7, 131.3, 130.6, 128.7, 127.6, 127.0, 124.6, 119.2, 113.1, 111.1, 68.1, 29.7, 16.4; HRMS (ESI-QTOF) m/z [M+H]⁺ calcd for C₁₆H₁₃Cl₂N₂O₃ 351.0298, found 351.0296.

Synthesis Example 14. Compound Represented by [Chemical Formula 18]

[Chemical Formula 18]

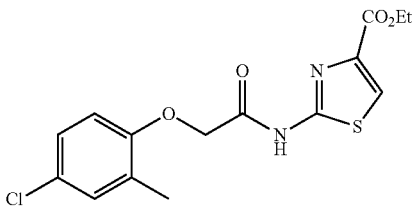

After adding 4-(ethoxycarbonyl)thiazol-2-aminium bromide (76 mg, 1.2 eq.), EDC-HCl (72 mg, 1.5 eq.), DMAP (1.5 mg, 0.05 eq.) and Et₃N (70 μL, 2 eq.) to a solution of 2-(4-chloro-2-methylphenoxy)acetic acid (50 mg, 0.25 mmol) in CH₂Cl₂ (1 mL) at 0° C. and stirring at room temperature for 16 hours, the reaction mixture was diluted with CH₂Cl₂ (2 mL) and washed with 15% HCl (1 mL). The aqueous layer was extracted once more with CH₂Cl₂ (2 mL) and the organic layer was dried with MgSO₄ and concentrated under reduced pressure. The obtained crude residue was purified by silica gel column chromatography (hexane:ethyl acetate:dichloroethane=10:1:2, volume ratio), affording a [Chemical Formula 18] compound as a white solid.

White solid, mp: 154.0-155.0° C.; ¹H NMR (400 MHz, CDCl₃) δ 9.79 (br s, 1H), 7.90 (s, 1H), 7.19 (s, 1H), 7.13 (dd, J=2.4, 8.8 Hz, 1H), 6.72 (d, J=8.8 Hz, 1H), 4.73 (s, 2H), 4.41 (q, J=7.2 Hz, 2H), 2.31 (s, 3H), 1.4 (t, J=7.0 Hz, 3H); ¹³C NMR (100 MHz, CDCl₃) δ 166.9, 161.4, 156.6, 153.7, 142.1, 131.4, 129.1, 127.7, 127.0, 122.9, 113.2, 67.8, 61.7, 16.5, 14.5; HRMS (ESI-QTOF) m/z [M+Na]⁺ calcd for C₁₅H₁₅ClN₂NaO4ₛ 377.0333, found 377.0331.

COMPARATIVE EXAMPLES

Comparative Synthesis Example 1. Compound Represented by [Chemical Formula 19]

[Chemical Formula 19]

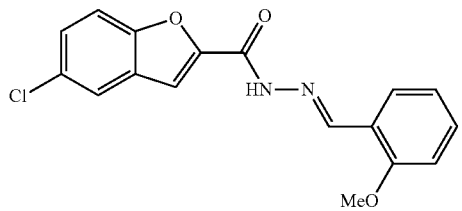

White solid, mp: 193.0-196.0° C.; ¹H NMR (400 MHz, DMSO-d₆) δ 12.22 (s, 1H), 8.87 (s, 1H), 7.93 (s, 1H), 7.88 (d, J=7.6 Hz, 1H), 7.77-7.70 (m, 2H), 7.51 (dd, J=2.0, 8.8 Hz, 1H), 7.44 (t, J=7.8 Hz, 1H), 7.11 (d, J=8.4 Hz, 1H), 7.03 (t, J=7.6 Hz, 1H), 3.88 (s, 3H); ¹³C NMR (100 MHz, DMSO-d₆) δ 157.9, 154.2, 152.9, 149.3, 144.3, 131.9, 128.6, 128.2, 127.1, 125.6, 122.3, 122.1, 120.8, 113.6, 111.9, 110.1, 55.7; HRMS (ESI-QTOF) m/z [M+H]⁺ calcd for C₁₇H₁₄ClN₂O₃ 329.0687, found 329.0688.

Comparative Synthesis Example 2. Compound Represented by [Chemical Formula 20]

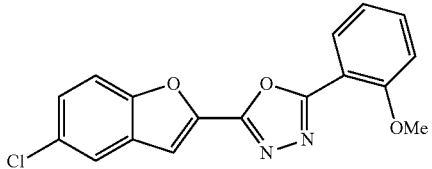

[Chemical Formula 20]

Light yellow solid, mp: 156.4-159.0° C.; $^1$H NMR (400 MHz, CDCl$_3$) δ 8.04 (d, J=7.6 Hz, 1H), 7.68 (d, J=1.6 Hz, 1H), 7.60-7.49 (m, 3H), 7.40 (dd, J=2.0, 8.8 Hz, 1H), 7.15-7.07 (m, 2H), 4.02 (s, 3H); $^{13}$C NMR (100 MHz, CDCl$_3$) δ 163.7, 158.2, 157.3, 154.1, 142.4, 133.7, 130.8, 129.8, 128.8, 127.4, 121.8, 121.0, 113.3, 112.4, 112.1, 109.3, 56.2; HRMS (ESI-QTOF) m/z [M+H]$^+$ calcd for C$_{17}$H$_{12}$ClN$_2$O$_3$ 327.0531, found 327.0532.

Comparative Synthesis Example 3. Compound Represented by [Chemical Formula 21]

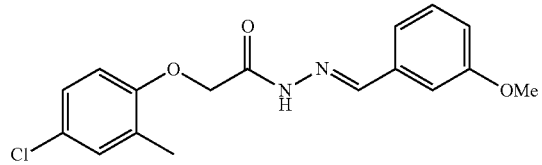

[Chemical Formula 21]

White solid, mp: 188.2-190.5° C.; $^1$H NMR (400 MHz, DMSO-d$_6$) δ 11.64 (s, 1H, isomer a), 11.55 (s, 1H, isomer b), 8.26 (s, 1H, isomer b), 7.97 (s, 1H, isomer a), 7.45-7.1 (m, 4H, isomer a, b), 7.0 (s, 1H, isomer a, b), 6.95-6.75 (m, 1H, isomer a, b), 5.18 (s, 2H, isomer a) 4.69 (s, 2H, isomer b), 3.78 (s, 3H, isomer a, b), 2.30-2.13 (m, 3H, isomer a, b); $^{13}$C NMR (100 MHz, DMSO-d$_6$) δ 169.0, 164.2, 159.5, 155.3, 154.9, 147.8, 143.7, 135.5, 135.4, 130.1, 130.0, 129.9, 128.8, 128.4, 126.4, 126.3, 124.5, 123.9, 120.1, 119.6, 116.4, 115.9, 113.2, 113.0, 111.5, 111.3, 66.9, 65.3, 55.2, 15.9; HRMS (ESI-QTOF) m/z [M+H]$^+$ calcd for C$_{17}$H$_{18}$ClN$_2$O$_3$ 333.1000, found 333.1003.

Comparative Synthesis Example 4. Compound Represented by [Chemical Formula 22]

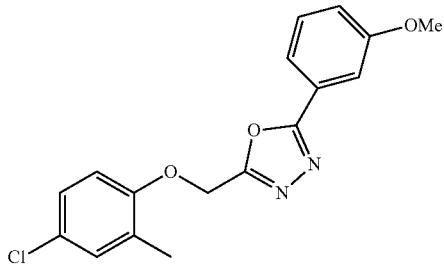

[Chemical Formula 22]

Light yellow solid, mp: 86.0-86.1° C.; $^1$H NMR (400 MHz, CDCl$_3$) δ 7.64 (d, J=7.6 Hz, 1H), 7.59 (s, 1H) 7.42 (t, J=8.0 Hz, 1H), 7.17-7.07 (m, 3H), 6.94 (d, J=9.2 Hz, 1H), 5.31 (s, 2H), 3.88 (s, 3H), 2.24 (s, 3H); $^{13}$C NMR (100 MHz, CDCl$_3$) δ 165.9, 162.3, 160.1, 154.5, 131, 130.4, 129.5, 126.9, 126.7, 124.6, 119.6, 118.7, 113.1, 111.8, 60.6, 55.7, 16.2; HRMS (ESI-QTOF) m/z [M+H]$^+$ calcd for C$_{17}$H$_{16}$ClN$_2$O$_3$ 331.0844, found 331.0845.

Comparative Synthesis Example 5. Compound Represented by [Chemical Formula 23]

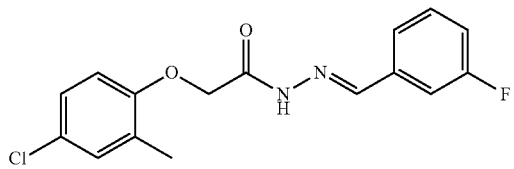

[Chemical Formula 23]

White solid, mp: 200.3-201.8° C.; $^1$H NMR (400 MHz, DMSO-d$_6$) δ 11.7 (s, 1H, isomer a, b), 8.29 (s, 1H, isomer b) 8.0 (s, 1H, isomer a), 7.61-7.43 (m, 3H, isomer a, b), 7.32-7.12 (m, 3H, isomer a, b), 6.91-6.85 (m, 1H, isomer a, b) 5.20 (s, 2H, isomer a), 4.70 (s, 2H, isomer b), 2.23 (s, 3H, isomer b), 2.2 (s, 3H, isomer a); $^{13}$C NMR (100 MHz, DMSO-d$_6$) δ 169.1, 164.3, 163.6, 161.2, 155.3, 154.9, 142.4, 136.6, 130.9, 130.8, 130.1, 129.9, 128.4, 126.4, 126.3, 123.9, 123.6, 116.8, 113.1, 112.9, 112.7, 66.9, 65.3, 15.9; HRMS (ESI-QTOF) m/z [M+H]$^+$ calcd for C$_{16}$H$_{15}$ClFN$_2$O$_2$ 321.0801, found 321.0806.

Comparative Synthesis Example 6. Compound Represented by [Chemical Formula 24]

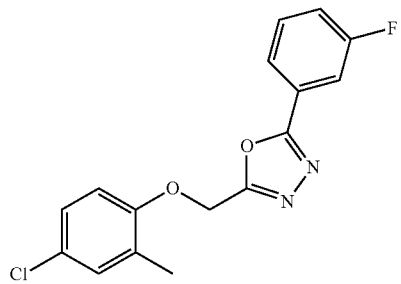

[Chemical Formula 24]

White solid, mp: 85.2-87.8° C.; $^1$H NMR (400 MHz, CDCl$_3$) δ 7.87 (d, J=8.0 Hz, 1H), 7.77 (d, J=9.2 Hz, 1H), 7.55-7.47 (m, 1H), 7.3-7.23 (m, 1H), 7.17-7.12 (m, 2H), 6.93 (d, J=8.4 Hz, 1H), 5.32 (s, 2H), 2.24 (s, 3H); $^{13}$C NMR (100 MHz, CDCl$_3$) δ 165.0, 164.96, 164.2, 162.6, 161.7, 154.5, 131.2, 131.1, 131.1, 129.5, 127.0, 126.7, 125.5, 125.4, 123.0, 122.98, 119.5, 119.3, 114.4, 114.2, 113.0, 60.5, 16.2; HRMS (ESI-QTOF) m/z [M+H]$^+$ calcd for C$_{16}$H$_{13}$ClFN$_2$O$_2$ 319.0644, found 319.0643.

Comparative Synthesis Example 7. Compound Represented by [Chemical Formula 25]

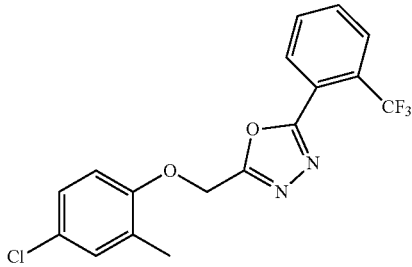

[Chemical Formula 25]

White solid, mp: 70.8-72.0° C.; $^1$H NMR (400 MHz, CDCl$_3$) δ 8.09-8.05 (m, 1H), 7.89-7.85 (m, 1H), 7.74-7.70 (m, 2H), 7.17-7.11 (m, 2H), 6.91 (d, J=8.4 Hz, 1H), 5.34 (s, 2H), 2.23 (s, 3H); $^{13}$C NMR (100 MHz, CDCl$_3$) δ 164.4, 163.5, 154.4, 132.4, 132.4, 132.1, 132.1, 132.1, 131.1, 129.6, 126.7, 112.8, 60.4, 16.1; HRMS (ESI-QTOF) m/z [M+H]$^+$ calcd for C$_{17}$H$_{13}$C$_l$F$_3$N$_2$O$_2$ 369.0612, found 369.0613.

Comparative Synthesis Example 8. Compound Represented by [Chemical Formula 26]

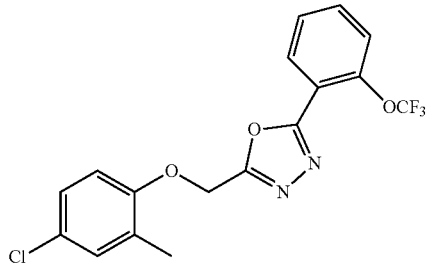

[Chemical Formula 26]

Light yellow solid, mp: 85.6-86.6° C.; $^1$H NMR (400 MHz, CDCl$_3$) δ 8.18 (d, J=7.2 Hz, 1H), 7.62 (t, J=7.2 Hz, 1H), 7.52-7.41 (m, 2H), 7.18-7.09 (m, 2H), 6.92 (d, J=8.0 Hz, 1H), 5.34 (s, 2H), 2.23 (s, 3H); $^{13}$C NMR (100 MHz, CDCl$_3$) δ 163.2, 163.0, 154.4, 146.6, 133.5, 131.0, 130.9, 129.5, 127.6, 126.9, 126.6, 122.5, 121.8, 119.2, 117.8, 112.8, 60.4, 16.0; HRMS (ESI-QTOF) m/z [M+H]$^+$ calcd for C$_{17}$H$_{13}$ClF$_3$N$_2$O$_3$ 385.0561, found 385.0563.

Comparative Synthesis Example 9. Compound Represented by [Chemical Formula 27]

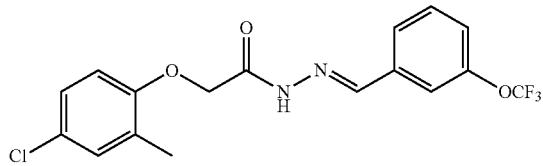

[Chemical Formula 27]

White solid, mp: 176.4-179.2° C.; $^1$H NMR (400 MHz, DMSO-d$_6$) δ 11.76 (s, 1H, isomer a), 11.70 (s, 1H, isomer b), 8.33 (s, 1H, isomer b), 8.03 (s, 1H, isomer a), 7.76-7.65 (m, 3H, isomer a), 7.62-7.53 (m, 3H, isomer b), 7.42 (t, J=8.4 Hz, 1H, isomer a, b), 7.28-7.12 (m, 3H, isomer a), 6.92-6.83 (m, 3H, isomer b), 5.20 (s, 2H, isomer a), 4.71 (s, 2H, isomer b), 2.24 (s, 3H, isomer b), 2.20 (s, 3H, isomer a); $^{13}$C NMR (100 MHz, DMSO-d$_6$) δ 169.2, 164.4, 155.2, 154.9, 148.8, 146.1, 142.1, 136.6, 136.5, 131.0, 130.8, 130.1, 129.9, 128.7, 128.4, 126.4, 126.4, 126.2, 124.5, 123.9, 122.5, 122.1, 121.3, 118.8, 118.7, 113.2, 113.1, 67.0, 65.3, 15.9; HRMS (ESI-QTOF) m/z [M+H]$^+$ calcd for C$_{17}$H$_{15}$ClF$_3$N$_2$O$_3$ 387.0718, found 387.0715.

Comparative Synthesis Example 10. Compound Represented by [Chemical Formula 28]

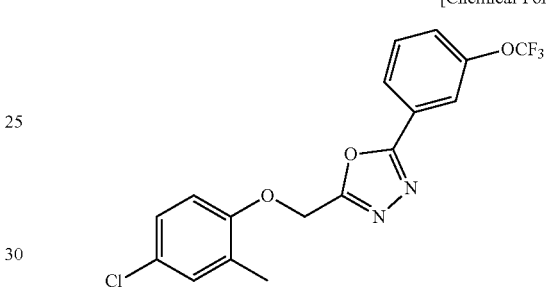

[Chemical Formula 28]

White solid, mp: 80.3-80.8° C.; $^1$H NMR (400 MHz, CDCl$_3$) δ 8.02 (d, J=8.0 Hz, 1H), 7.93 (s, 1H), 7.58 (t, J=8.0 Hz, 1H), 7.42 (d, J=8.4 Hz, 1H), 7.17-7.10 (m, 2H), 6.94 (d, J=8.0 Hz, 1H), 5.33 (s, 2H), 2.24 (s, 3H); $^{13}$C NMR (100 MHz, CDCl$_3$) δ 164.7, 162.7, 154.4, 149.8, 131.1, 131.0, 129.5, 127.1, 126.7, 125.5, 125.4, 124.6, 121.8, 119.7, 113.0, 60.5, 16.2; HRMS (ESI-QTOF) m/z [M+H]$^+$ calcd for C$_{17}$H$_{13}$ClF$_3$N$_2$O$_3$ 385.0561, found 385.0568.

Comparative Synthesis Example 11. Compound Represented by [Chemical Formula 29]

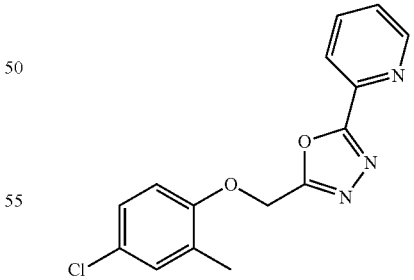

[Chemical Formula 29]

White solid, mp: 118.3-120.0° C.; 1H NMR (400 MHz, CDCl$_3$) δ 8.80 (d, J=4.4 Hz, 1H), 8.27 (d, J=8.0 Hz, 1H), 7.95-7.87 (m, 1H), 7.50 (dd, J=5.2, 6.8 Hz, 1H), 7.16-7.10 (m, 2H), 6.94 (d, J=9.2 Hz, 1H), 5.35 (s, 2H), 2.23 (s, 3H); $^{13}$C NMR (100 MHz, CDCl$_3$) δ 164.9, 163.1, 154.3, 150.4, 143.1, 137.3, 130.9, 129.4, 126.7, 126.5, 126.2, 123.4, 112.7, 60.2, 16.1; HRMS (ESI-QTOF) m/z [M+H]$^+$ calcd for C$_{15}$H$_{13}$ClN$_3$O$_2$ 302.0691, found 302.0690.

Comparative Synthesis Example 12. Compound Represented by [Chemical Formula 30]

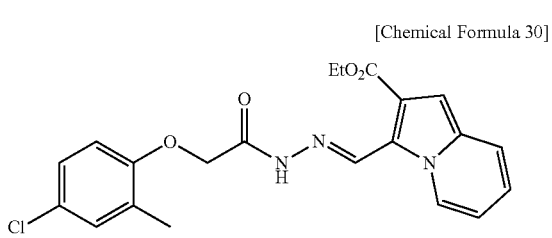 [SMILES: CCOC(=O)c1cc2ccccn2c1/C=N/NC(=O)COc1ccc(Cl)cc1C]

[Chemical Formula 30]

Yellow solid, mp: 169.0-170.2° C.; 1H NMR (400 MHz, DMSO-$d_6$) δ 11.81 (s, 1H, isomer b), 11.74 (s, 1H, isomer a), 9.70 (d, J=6.8 Hz, 1H, isomer b), 9.32 (d, J=6.4 Hz, 1H, isomer a), 9.21 (s, 1H, isomer b), 9.00 (s, 1H, isomer a), 7.73 (t, J=8 Hz, 1H, isomer a, b), 7.28-6.84 (m, 6H, isomer a, b), 5.24 (s, 2H, isomer a), 4.73 (s, 2H, isomer b), 4.38-4.27 (m, 2H, isomer a, b), 2.29-2.15 (m, 3H, isomer a, b) 1.41-1.28 (m, 3H, isomer a, b); $^{13}$C NMR (100 MHz, DMSO-de) δ 168.4, 163.8, 155.3, 155.0, 140.1, 137.1, 134.5, 134.4, 130.1, 129.9, 128.2, 127.7, 126.4, 126.3, 121.7, 121.5, 120.2, 115.0, 113.2, 113.0, 104.1, 104.0, 66.9, 65.5, 60.5, 16.0, 14.2; HRMS (ESI-QTOF) m/z [M+H]$^+$ calcd for $C_{21}H_{21}ClN_3O_4$ 414.1215, found 414.1218.

Comparative Synthesis Example 13. Compound Represented by [Chemical Formula 31]

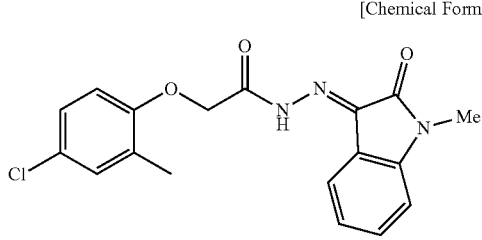

[Chemical Formula 31]

Yellow solid, mp: 209.3-210.8° C.; 1H NMR (400 MHz, CDCl$_3$) δ 13.81 (s, 1H, isomer a), 12.63 (s, 1H, isomer b), 7.83 (d, J=7.6 Hz, 2H, isomer a), 7.58 (d, J=7.2 Hz, 2H, isomer b), 7.41 (t, J=7.6 Hz, 1H, isomer a, b), 7.22-7.11 (m, 3H, isomer a, b), 6.88 (d, J=8 Hz, 1H, isomer a, b), 6.74 (d, J=8.4 Hz, 1H, isomer a, b), 5.24 (s, 2H, isomer b), 4.75 (s, 2H, isomer a), 3.27 (s, 3H, isomer a, b), 2.44 (s, 3H, isomer a), 2.31 (s, 1H, isomer b); $^{13}$C NMR (100 MHz, CDCl$_3$) δ 166.1, 161.2, 153.9, 144.1, 138.9, 132.2, 131.2, 129.4, 126.9, 126.7, 123.7, 123.6, 122.4, 121.0, 119.5, 112.1, 109.1, 67.5, 66.0, 26.0, 25.6, 16.6, 16.4; HRMS (ESI-QTOF) m/z [M+H]$^+$ calcd for $C_{18}H_{17}ClN_3O_3$ 358.0953, found 358.0958.

Comparative Synthesis Example 14. Compound Represented by [Chemical Formula 32]

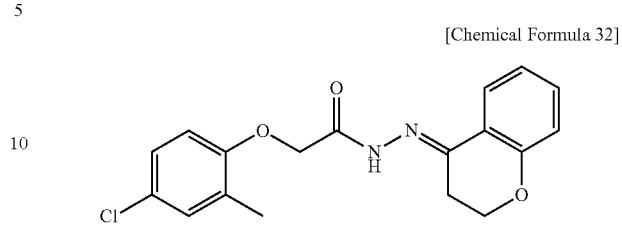

[Chemical Formula 32]

White solid, mp: 215.4-217.5° C.; 1H NMR (400 MHz, DMSO-$d_6$) δ 11.96 (s, 1H, isomer a), 10.62 (s, 1H, isomer b), 8.00-7.92 (m, 1H, isomer a, b), 7.35-7.12 (m, 3H, isomer a, b), 7.03-6.95 (m, 1H, isomer a, b), 6.90 (d, J=7.6 Hz, 2H, isomer, a), 6.83 (d, J=8.4 Hz, 2H, isomer b), 5.23 (s, 2H, isomer a), 4.76 (s, 2H, isomer b), 4.31-4.20 (m, 2H, isomer a, b), 2.89-2.80 (m, 2H, isomer a, b), 2.22 (s, 3H, isomer a, b); $^{13}$C NMR (100 MHz, DMSO-$d_6$) δ 169.6, 164.1, 157.1, 156.9, 155.3, 154.9, 147.9, 142.8, 131.4, 131.0, 130.1, 129.9, 128.5, 128.3, 126.4, 126.2, 124.8, 124.7, 124.3, 123.9, 121.3, 120.3, 117.5, 117.4, 113.0, 66.5, 65.6, 64.5, 25.6, 25.1, 16.0; HRMS (ESI-QTOF) m/z [M+Na]$^+$ calcd for $C_{18}H_{17}ClN_3NaO_2$ 367.0820, found 367.0824.

Comparative Synthesis Example 15. Compound Represented by [Chemical Formula 33]

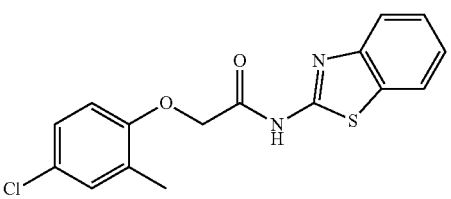

[Chemical Formula 33]

White solid, mp: 167.3-170.9° C.; 1H NMR (400 MHz, CDCl$_3$) δ 9.70 (br s, 1H), 7.84 (d, J=8.0 Hz, 1H), 7.81 (d, J=8.4 Hz, 1H), 7.47 (t, J=7.6 Hz, 1H), 7.35 (t, J=7.6 Hz, 1H), 7.20 (s, 1H), 7.15 (d, J=8.8 Hz, 1H), 6.75 (d, J=8.8 Hz, 1H), 4.74 (s, 2H), 2.35 (s, 3H); $^{13}$C NMR (100 MHz, CDCl$_3$) δ 166.7, 156.4, 153.7, 148.4, 131.4, 129.0, 127.1, 126.6, 124.5, 121.6, 121.5, 113.1, 67.7, 16.5; HRMS (ESI-QTOF) m/z [M+H]$^+$ calcd for $C_{16}H_{14}ClN_2O_2S$ 333.0459, found 333.0461.

Comparative Synthesis Example 16. Compound Represented by [Chemical Formula 34]

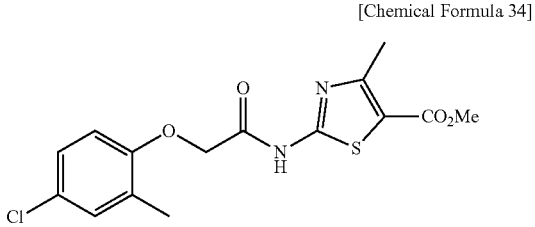 [SMILES: COC(=O)c1sc(NC(=O)COc2ccc(Cl)cc2C)nc1C]

[Chemical Formula 34]

White solid, mp: 202.8-204.0° C.; 1H NMR (400 MHz, CDCl$_3$) δ 9.55 (br s, 1H), 7.20 (s, 1H), 7.15 (dd, J=2.0, 8.8 Hz, 1H), 6.73 (d, J=8.4 Hz, 1H), 4.72 (s, 2H), 3.87 (s, 3H), 2.66 (s, 3H), 2.33 (s, 3H); $^{13}$C NMR (100 MHz, CDCl$_3$) δ 166.4, 163.1, 157.8, 156.9, 153.6, 131.4, 128.9, 127.8, 127.1, 116.6, 113.2, 67.7, 52.1, 17.3, 16.5; HRMS (ESI-QTOF) m/z [M+H]$^+$ calcd for C$_{15}$H$_{16}$ClN$_2$O$_4$ 355.0514, found 355.0513.

Comparative Synthesis Example 17. Compound Represented by [Chemical Formula 35]

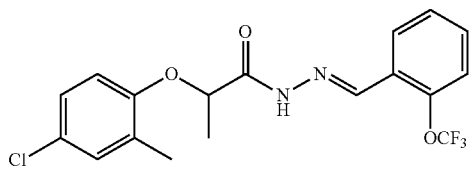

[Chemical Formula 35]

White solid, mp: 147.5-149.1° C.; $^1$H NMR (400 MHz, CDCl$_3$) δ 9.55 (s, 1H, isomer a), 9.15 (s, 1H, isomer b), 8.38 (s, 1H, isomer a), 8.20 (d, J=7.6 Hz, 1H, isomer a), 8.02 (s, 1H, isomer b), 7.84 (d, J=7.6 Hz, 1H, isomer b), 7.49-7.41 (m, 1H, isomer a, b), 7.36-7.30 (m, 1H, isomer a, b), 7.28-7.23 (m, 1H, isomer a, b), 7.19 (s, 1H, isomer a), 7.15-7.08 (m, 1H, isomer a, b), 7.02 (dd, J=8.6 Hz, 1H, isomer b), 6.78 (d, J=8.8 Hz, 1H, isomer a), 6.63 (d, J=8.4 Hz, 1H, isomer b), 5.55 (q, J=6.8 Hz, 1H, isomer b), 4.78 (q, J=6.8 Hz, 1H, isomer a), 2.31 (s, 3H, isomer a), 2.27 (s, 3H, isomer b), 1.71 (d, J=6.8 Hz, 3H, isomer b), 1.67 (d, J=6.8 Hz, 3H, isomer a); 13C NMR (100 MHz, CDCl$_3$) δ 173.0, 168.4, 153.7, 142.9, 132.0, 131.7, 131.3, 130.9, 129.6, 127.9, 127.4, 127.35, 127.3, 127.2, 127.1, 126.3, 126.2, 120.9, 114.8, 76.3, 71.5, 19.0, 18.1, 16.6, 16.4; HRMS (ESI-QTOF) m/z [M+H]$^+$ calcd for C$_{18}$H$_{17}$ClF$_3$N$_2$O$_3$ 401.0874, found 401.0873.

Comparative Synthesis Example 18. Compound Represented by [Chemical Formula 36]

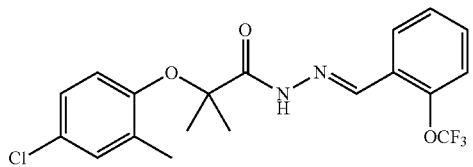

[Chemical Formula 36]

White solid, mp: 175.8-178.2° C.; $^1$H NMR (400 MHz, CDCl$_3$) δ 9.93 (s, 1H), 8.42 (s, 1H), 8.21 (dd, J=1.2, 7.6 Hz, 1H), 7.43 (t, J=7.0 Hz, 1H), 7.33 (t, J=7.6 Hz, 1H), 7.26 (m, 1H), 7.18 (d, J=2.0 Hz, 1H), 7.05 (dd, J=2.4, 8.8 Hz, 1H), 6.81 (d, J=8.8 Hz, 1H), 2.26 (s, 3H), 1.61 (s, 6H); $^{13}$C NMR (100 MHz, CDCl$_3$) δ 171.3, 151.2, 147.8, 142.3, 132.7, 131.8, 131.3, 128.4, 127.8, 127.3, 126.6, 126.4, 121.8, 121.0, 120.9, 119.2, 82.2, 25.3, 17.1; HRMS (ESI-QTOF) m/z [M+H]$^+$ calcd for C$_{19}$H$_{19}$ClF$_3$N$_2$O$_3$ 415.1031, found 415.1035.

Comparative Synthesis Example 19. Compound Represented by [Chemical Formula 37]

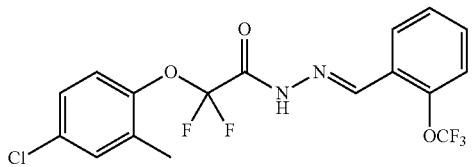

[Chemical Formula 37]

White solid, mp: 167.4-170.2° C.; $^1$H NMR (400 MHz, CDCl$_3$) δ 9.53 (s, 1H), 8.58 (s, 1H), 8.23 (d, J=7.6 Hz, 1H), 7.51 (t, J=7.0 Hz, 1H), 7.38 (t, J=7.6 Hz, 1H), 7.30 (d, J=8.0 Hz, 1H), 7.28-7.25 (m, 1H), 7.19 (s, 2H), 2.32 (s, 3H); 13C NMR (100 MHz, CDCl$_3$) δ 155.6, 155.2, 148.0, 146.0, 145.3, 133.4, 132.5, 132.1, 131.3, 127.9, 127.3, 127.0, 125.5, 123.4, 120.9, 114.6, 16.5; HRMS (ESI-QTOF) m/z [M+H]$^+$ calcd for C$_{17}$H$_{13}$ClF$_5$N$_2$O$_3$ 423.0529, found 423.0527.

TEST EXAMPLES

Test Example 1. Selective Inhibition of ANO1 Over ANO2

TABLE 1

| | Structure | IC$_{50}$ (μM) of ANO1 | IC$_{50}$ (μM) of ANO2 |
|---|---|---|---|
| Control [Ani9] | 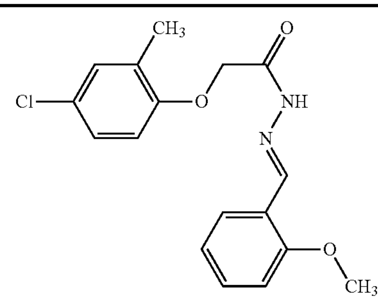 | 0.097 ± 0.01 | >100 |

TABLE 1-continued

| | Structure | IC$_{50}$ (μM) of ANO1 | IC$_{50}$ (μM) of ANO2 |
|---|---|---|---|
| Example 1 [Chemical Formula 5] | 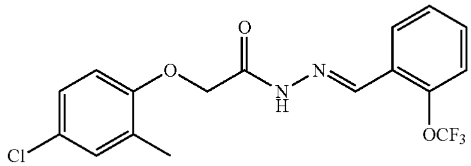 [SMILES: Cc1cc(Cl)ccc1OCC(=O)N/N=C/c1ccccc1OC(F)(F)F] | 0.021 ± 0.005 | NA |
| Example 2 [Chemical Formula 6] | 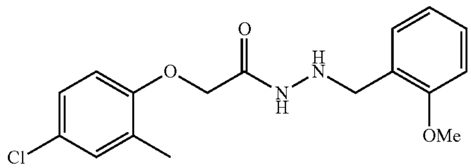 [SMILES: COc1ccccc1CNNC(=O)COc1ccc(Cl)cc1C] | 10.7 ± 0.14 | >100 |
| Example 3 [Chemical Formula 7] | 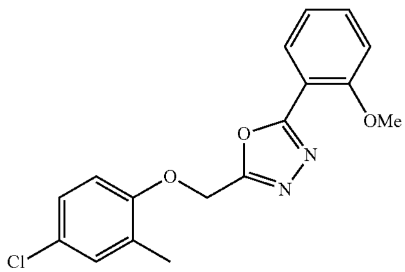 [SMILES: COc1ccccc1-c1nnc(COc2ccc(Cl)cc2C)o1] | 19.4 ± 0.01 | 12.4 ± 0.05 |
| Example 4 [Chemical Formula 8] | 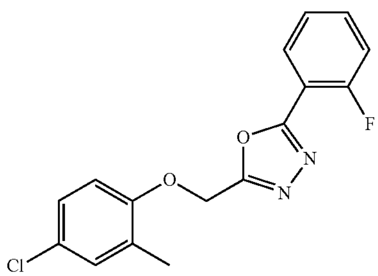 [SMILES: Cc1cc(Cl)ccc1OCc1nnc(-c2ccccc2F)o1] | 21.2 ± 0.17 | >100 |
| Example 5 [Chemical Formula 9] | 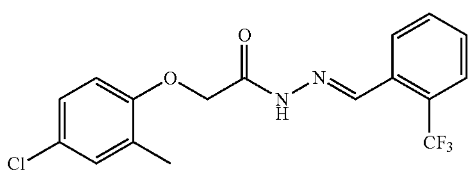 [SMILES: Cc1cc(Cl)ccc1OCC(=O)N/N=C/c1ccccc1C(F)(F)F] | 0.21 ± 0.04 | NA |
| Example 6 [Chemical Formula 10] | 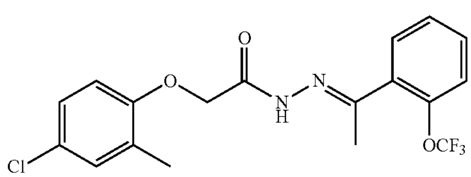 [SMILES: C/C(=N\NC(=O)COc1ccc(Cl)cc1C)c1ccccc1OC(F)(F)F] | 0.3 ± 0.02 | >100 |
| Example 7 [Chemical Formula 11] | 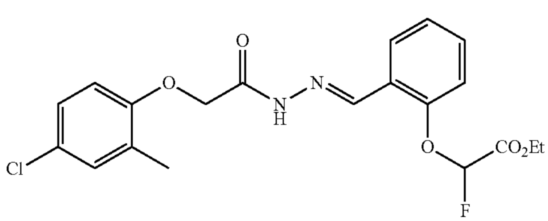 [SMILES: CCOC(=O)C(F)Oc1ccccc1/C=N/NC(=O)COc1ccc(Cl)cc1C] | 15.7 ± 0.01 | 59.4 ± 0.45 |

TABLE 1-continued

| | Structure | IC$_{50}$ (μM) of ANO1 | IC$_{50}$ (μM) of ANO2 |
|---|---|---|---|
| Example 8 [Chemical Formula 12] | 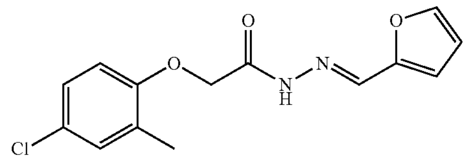 [SMILES: Cc1cc(Cl)ccc1OCC(=O)N/N=C/c1ccco1] | 25.7 ± 0.01 | NA |
| Example 9 [Chemical Formula 13] | 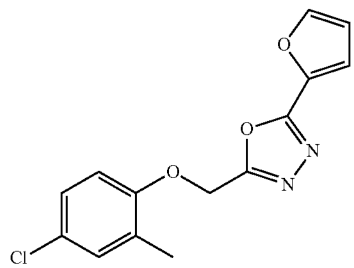 [SMILES: Cc1cc(Cl)ccc1OCc1nnc(-c2ccco2)o1] | 63.8 ± 0.02 | >100 |
| Example 10 [Chemical Formula 14] | 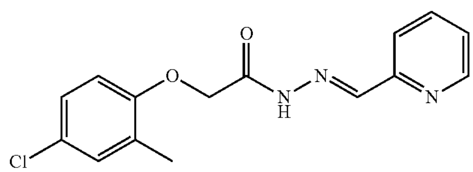 [SMILES: Cc1cc(Cl)ccc1OCC(=O)N/N=C/c1ccccn1] | 31.3 ± 0.57 | >100 |
| Example 11 [Chemical Formula 15] | 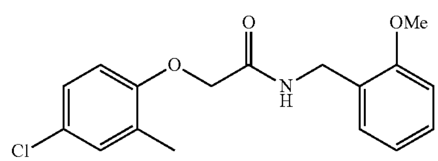 [SMILES: COc1ccccc1CNC(=O)COc1ccc(Cl)cc1C] | 20.6 ± 0.02 | 13.1 ± 0.07 |
| Example 12 [Chemical Formula 16] | 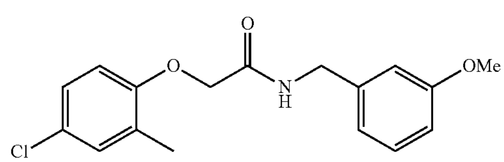 [SMILES: COc1cccc(CNC(=O)COc2ccc(Cl)cc2C)c1] | 53.7 ± 0.05 | >100 |
| Example 13 [Chemical Formula 17] | 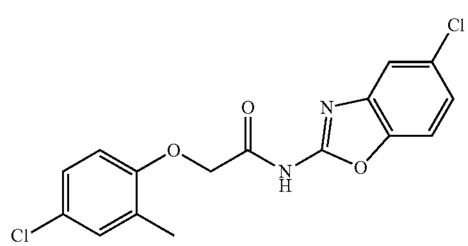 [SMILES: Cc1cc(Cl)ccc1OCC(=O)Nc1nc2cc(Cl)ccc2o1] | 14.2 ± 0.07 | NA |
| Example 14 [Chemical Formula 18] | 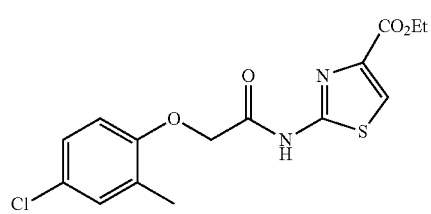 [SMILES: CCOC(=O)c1csc(NC(=O)COc2ccc(Cl)cc2C)n1] | 14.8 ± 0.01 | >100 |

TABLE 1-continued

| | Structure | IC$_{50}$ (μM) of ANO1 | IC$_{50}$ (μM) of ANO2 |
|---|---|---|---|
| Comparative Example 1 [Chemical Formula 19] | 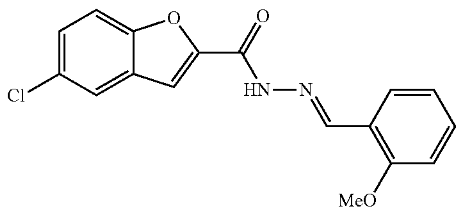 [SMILES: COc1ccccc1/C=N/NC(=O)c1cc2cc(Cl)ccc2o1] | >100 | >100 |
| Comparative Example 2 [Chemical Formula 20] | 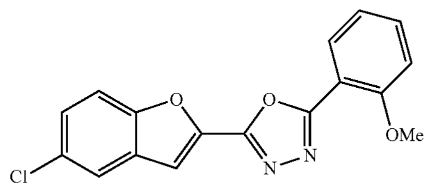 [SMILES: COc1ccccc1-c1nnc(-c2cc3cc(Cl)ccc3o2)o1] | >100 | >100 |
| Comparative Example 3 [Chemical Formula 21] | 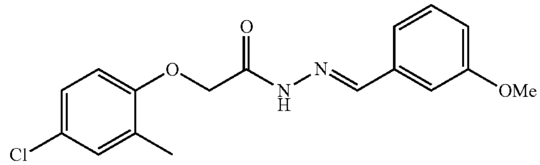 [SMILES: COc1cccc(/C=N/NC(=O)COc2ccc(Cl)cc2C)c1] | >100 | NA |
| Comparative Example 4 [Chemical Formula 22] | 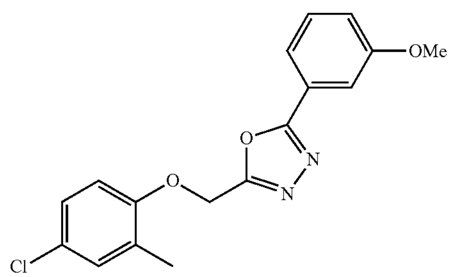 [SMILES: COc1cccc(-c2nnc(COc3ccc(Cl)cc3C)o2)c1] | >100 | >100 |
| Comparative Example 5 [Chemical Formula 23] | 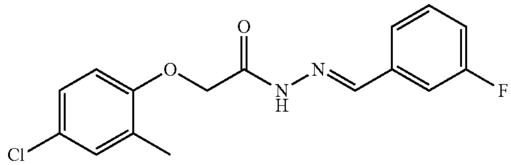 [SMILES: Cc1cc(Cl)ccc1OCC(=O)N/N=C/c1cccc(F)c1] | >100 | NA |
| Comparative Example 6 [Chemical Formula 24] | 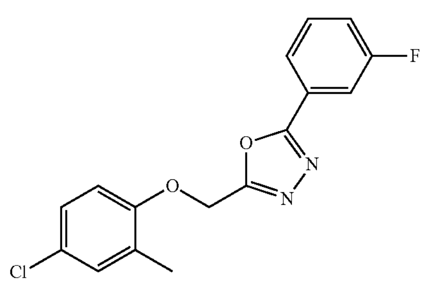 [SMILES: Cc1cc(Cl)ccc1OCc1nnc(-c2cccc(F)c2)o1] | >100 | >100 |
| Comparative Example 7 [Chemical Formula 25] | 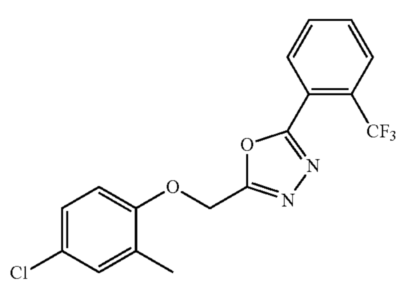 [SMILES: Cc1cc(Cl)ccc1OCc1nnc(-c2ccccc2C(F)(F)F)o1] | >100 | >100 |

TABLE 1-continued

| | Structure | IC$_{50}$ (μM) of ANO1 | IC$_{50}$ (μM) of ANO2 |
|---|---|---|---|
| Comparative Example 8 [Chemical Formula 26] | 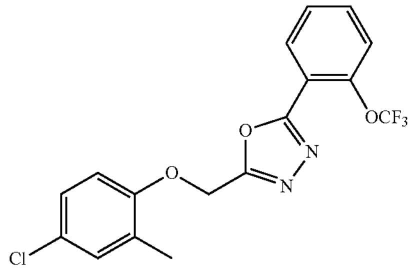 [SMILES: Cc1cc(Cl)ccc1OCc1nnc(-c2ccccc2OC(F)(F)F)o1] | >100 | NA |
| Comparative Example 9 [Chemical Formula 27] | 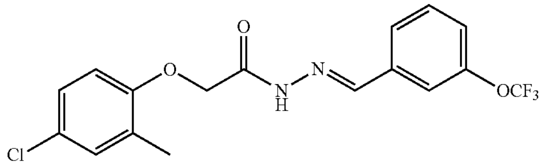 [SMILES: Cc1cc(Cl)ccc1OCC(=O)N/N=C/c1cccc(OC(F)(F)F)c1] | >100 | NA |
| Comparative Example 10 [Chemical Formula 28] | 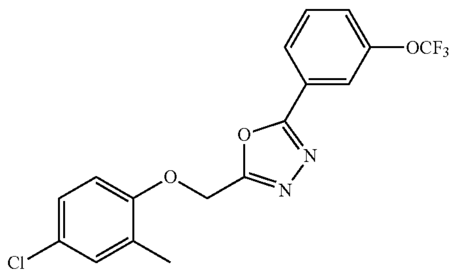 [SMILES: Cc1cc(Cl)ccc1OCc1nnc(-c2cccc(OC(F)(F)F)c2)o1] | >100 | NA |
| Comparative Example 11 [Chemical Formula 29] | 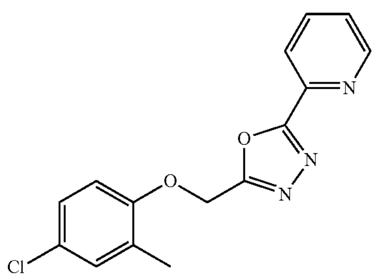 [SMILES: Cc1cc(Cl)ccc1OCc1nnc(-c2ccccn2)o1] | >100 | NA |
| Comparative Example 12 [Chemical Formula 30] | 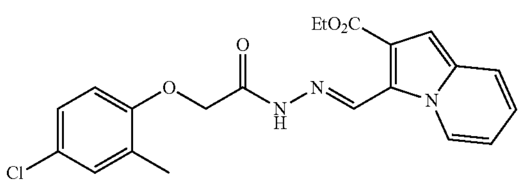 [SMILES: CCOC(=O)c1cc2ccccn2c1/C=N/NC(=O)COc1ccc(Cl)cc1C] | >100 | >100 |
| Comparative Example 13 [Chemical Formula 31] | 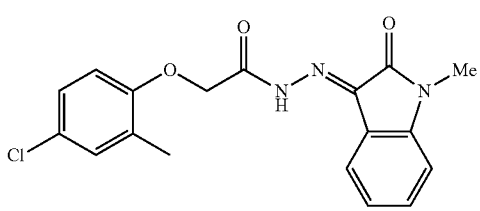 [SMILES: Cc1cc(Cl)ccc1OCC(=O)N/N=C1/C(=O)N(C)c2ccccc21] | >100 | NA |
| Comparative Example 14 [Chemical Formula 32] | 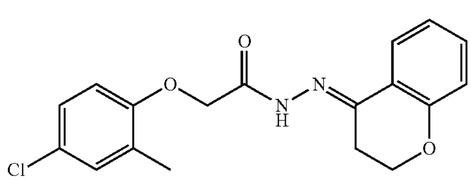 [SMILES: Cc1cc(Cl)ccc1OCC(=O)N/N=C1\CCOc2ccccc21] | >100 | NA |

TABLE 1-continued

| | Structure | IC$_{50}$ (μM) of ANO1 | IC$_{50}$ (μM) of ANO2 |
|---|---|---|---|
| Comparative Example 15 [Chemical Formula 33] | 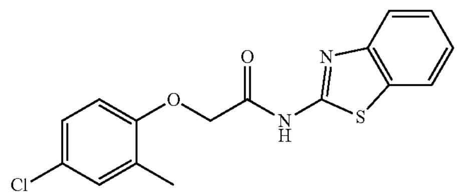 [SMILES: Cc1cc(Cl)ccc1OCC(=O)Nc1nc2ccccc2s1] | >100 | >100 |
| Comparative Example 16 [Chemical Formula 34] | 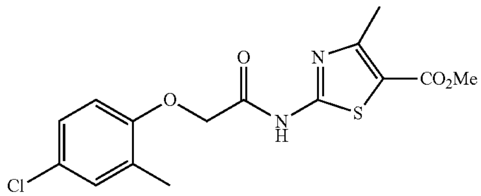 [SMILES: COC(=O)c1sc(NC(=O)COc2ccc(Cl)cc2C)nc1C] | >100 | NA |
| Comparative Example 17 [Chemical Formula 35] | 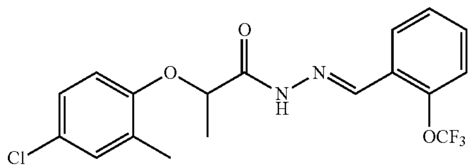 [SMILES: Cc1cc(Cl)ccc1OC(C)C(=O)N/N=C/c1ccccc1OC(F)(F)F] | >100 | NA |
| Comparative Example 18 [Chemical Formula 36] | 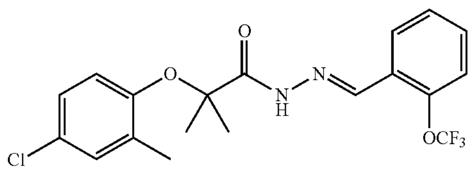 [SMILES: Cc1cc(Cl)ccc1OC(C)(C)C(=O)N/N=C/c1ccccc1OC(F)(F)F] | NA | >100 |
| Comparative Example 19 [Chemical Formula 37] | 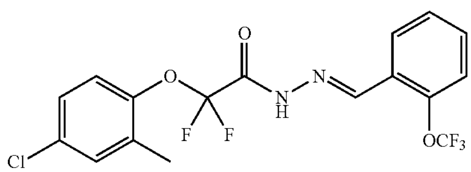 [SMILES: Cc1cc(Cl)ccc1OC(F)(F)C(=O)N/N=C/c1ccccc1OC(F)(F)F] | >100 | >100 |

As seen from Table 1, it was confirmed that the compounds of Examples 1-14 showed superior inhibitory activity selectively for ANO1 over ANO2. In contrast, the compounds of Comparative Examples 1-19 showed no inhibitory activity for ANO1 or ANO2.

In particular, the compound of Example 1 (Chemical Formula 5), which is an acylhydrazone having a trifluoromethoxy group at the ortho position showed the strongest ANO1 inhibitory activity, whereas the compound of Comparative Example 9 (Chemical Formula 27) having a trifluoromethoxy group at the meta position was found not to inhibit ANO1. This suggests that the orientation of the functional moiety is important.

In addition, it was confirmed that the compound of Example 6 (Chemical Formula 10) showed slightly weaker inhibitory activity than the compound of Example 1 (Chemical Formula 5).

Test Example 2. Investigation of Effect of [Chemical Formula 5] Compound of Inhibiting Activity of ANO1 Selectively Over CFTR or ANO2 Through Measurement of Short-Circuit Current FIG. 1A shows the effect of the [Chemical Formula 5] compound of inhibiting the activity of ANO1 (TMEM16A).

Specifically, Fischer rat thyroid (FRT) cells expressing ANO1 were differentiated by culturing in DMEM/Ham's F12 medium in Transwell for 5 days and then short-circuit current was measured using an Ussing chamber. Then, a regular $HCO^{3-}$ solution (120 mM NaCl, 5 mM KCl, 1 mM MgCl$_2$, 2.5 mM HEPES, 1 mM CaCl$_2$, 10 mM glucose, 25 mM NaHCO$_3$) was added to a basolateral bath of the Ussing chamber, and a luminal bath was stabilized for 20 minutes by creating a Cl$^-$ gradient by maintaining at 70 mM Cl$^-$. Then, after treating with the [Chemical Formula 5] compound at different concentrations (0, 0.003, 0.01, 0.03, 0.1, 0.3, 1.0 μM) and carrying out reaction for 20 minutes, ATP (100 μM) was added and the inhibitory effect for Cl$^-$ secretion was measured through ANO1 activity.

Figure 1B:
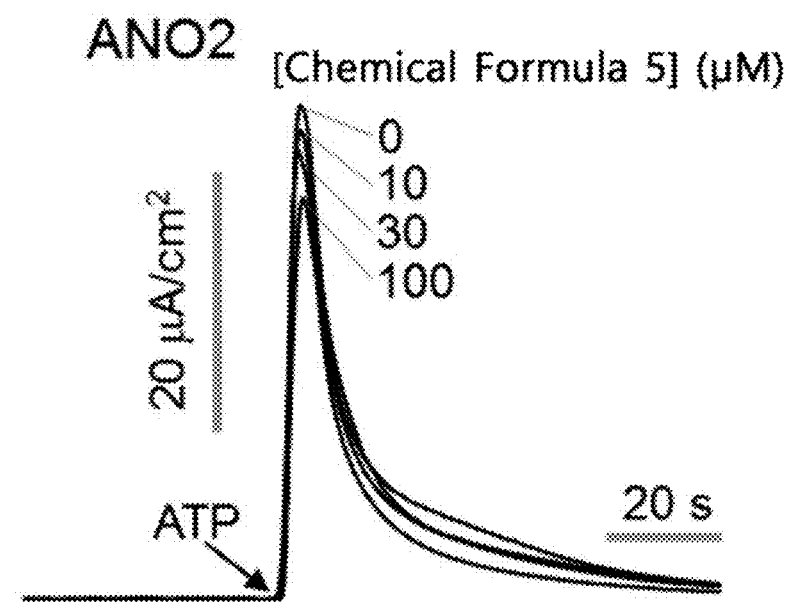
FIG. 1B shows a result of measuring the apical membrane current of FRT cells expressing ANO2.

FIG. 1B shows a result of differentiating Fischer rat thyroid (FRT) cells expressing ANO2 by culturing in DMEM/Ham's F12 medium in Transwell for 6 days, measuring short-circuit current, creating a Cl$^-$ gradient for 20 minutes with a regular $HCO^{3-}$ solution, treating with the [Chemical Formula 5] compound at different concentrations (0, 10, 30, 100 μM), carrying out reaction for 20 minutes, and then measuring the inhibitory effect for Cl$^-$ secretion through ANO2 activity by adding ATP (100 μM).

Figure 1C:
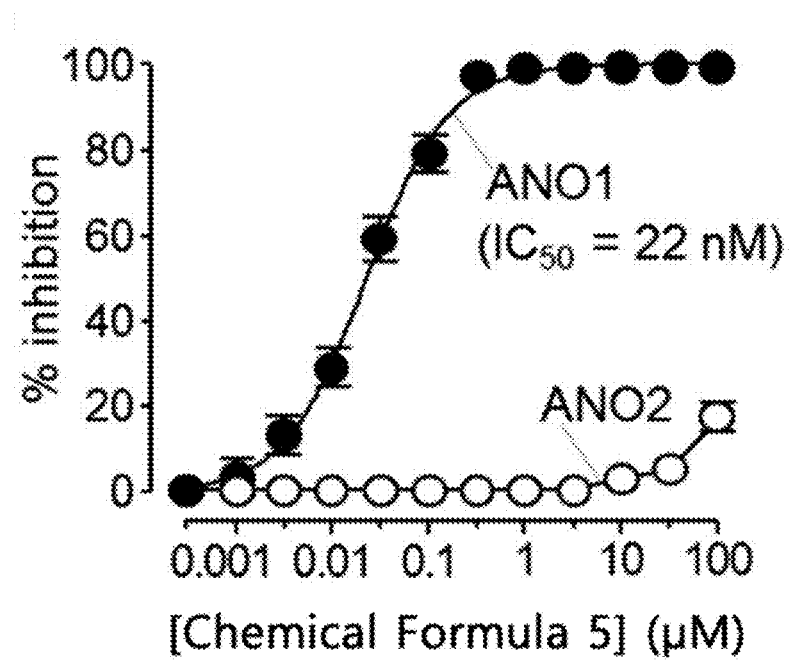
FIG. 1C shows inhibitory activity depending on the concentration of a [Chemical Formula 5] compound.

FIG. 1C shows the inhibitory effect for Cl$^-$ secretion of the [Chemical Formula 5] compound for ANO1 and ANO2 measured from the short-circuit current, represented as dose response curves using GraphPad Prism.

Figure 1D:
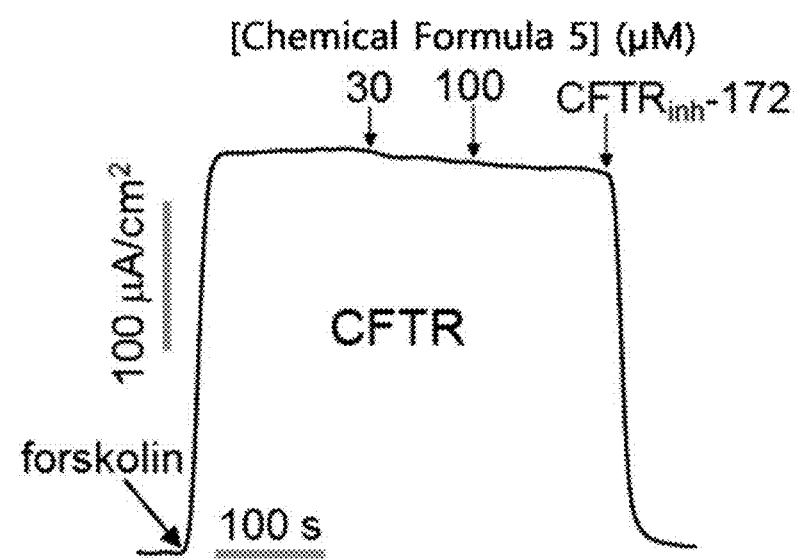
FIG. 1D shows a result of measuring the apical membrane current of FRT cells expressing human WT-CFTR (CFTR was activated with 20 μM forskolin, and the [Chemical Formula 5] compound of the indicated concentrations was used. CFTR was completely inhibited by 10 μM $CFTR_{inh}$-172.).

And, FIG. 1D shows a result of differentiating Fischer rat thyroid (FRT) cells expressing CFTR by culturing in DMEM/Ham's F12 medium in Transwell for 6 days, measuring short-circuit current, creating a Cl⁻ gradient for 20 minutes with a regular $HCO^{3-}$ solution, activating CFTR channels by treating with 10 μM forskolin, treating with the [Chemical Formula 5] compound at 30 or 100 μM, and inhibiting the migration of Cl⁻ by adding 10 μM $CFTR_{inh}$-172.

As seen from FIGS. 1A to 1D, it was confirmed that the [Chemical Formula 5] compound of the present disclosure strongly (4 times or higher) inhibits the activity of ANO1 as compared to the existing Ani9 compound (CAS Registry Number: 356102-14-2) ([Chemical Formula 5] compound: $IC_{50}$ 22 nM). Meanwhile, 100 μM of the [Chemical Formula 5] compound inhibited the activity of ANO2, which is much similar to ANO1 in structure, by 17.1% only.

In addition, it was confirmed that 100 μM of the [Chemical Formula 5] compound did not inhibit the activity of CFTR which secretes Cl⁻.

These results show that the [Chemical Formula 5] compound selectively inhibits the activity of ANO1, 1000 times or higher, over the activity of ANO2 or CFTR.

Figure 2A:
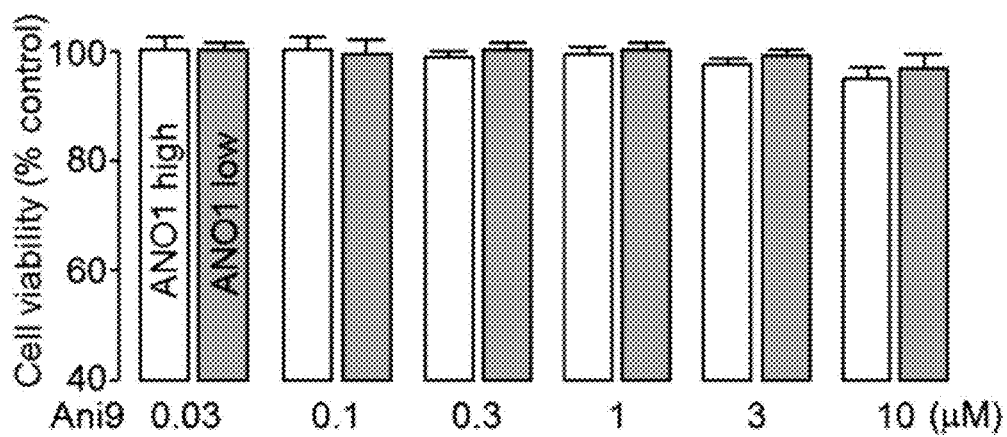
FIGS. 2A to 2C show a result of measuring the cell viability of PC-3 (prostate cancer cells) expressing ANO1 at high or low level depending on the concentration of Ani9, a [Chemical Formula 5] compound and a [Chemical Formula 27] compound.
Figure 2B:
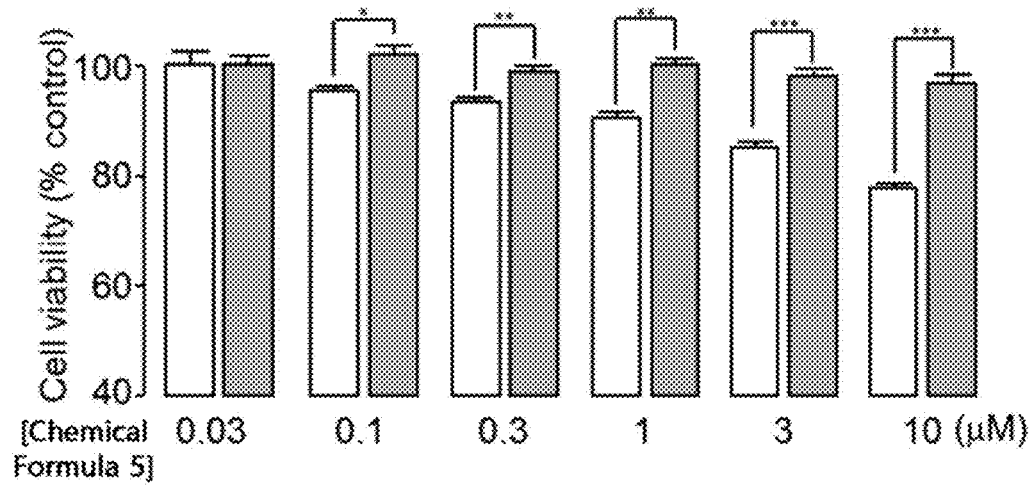
Figure 2C:
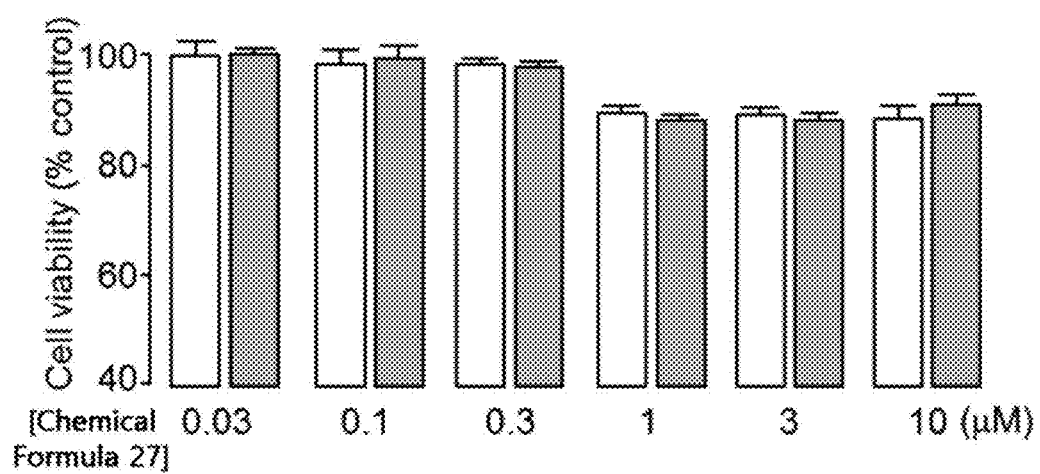

Test Example 3. Investigation of Inhibitory Effect of [Chemical Formula 5] Compound on PC-3 (Prostate Cancer) Cellular Growth FIGS. 2A to 2C show a result of measuring the cell viability of PC-3 prostate cancer cells expressing ANO1 at high or low level depending on the concentration of Ani9, the [Chemical Formula 5] compound and the [Chemical Formula 27] compound. The cell viability was determined by the MTS assay (mean±S.E., n=4; * P<0.05,  P<0.01, * P<0.001).

In FIG. 2A, PC-3 cells highly expressing ANO1 and PC-3 cells not expressing ANO1 were cultured on a 96-well micro plate, with about 5×10³ cells per each, and, 24 hours later, were treated with Ani9 at different concentrations (0.03, 0.1, 1, 3, 10 μM). 24 hours later, after adding 20 μL of an MTS solution to each well and culturing at 37° C. for 30 minutes under 5% $CO_2$, absorbance was measured at 490 nm using a microplate reader.

In FIG. 2B, PC-3 cells were treated with the [Chemical Formula 5] compound at different concentrations in the same manner as in FIG. 2A. In FIG. 2C, PC-3 cells were treated with the [Chemical Formula 27] compound, which is structurally very similar to the [Chemical Formula 5] compound but does not inhibit the activity of ANO1, at different concentrations. After adding 20 μL of an MTS solution to each well and culturing at 37° C. for 30 minutes under 5% $CO_2$, absorbance was measured at 490 nm using a microplate reader.

As seen from FIGS. 2A to 2C, the MTS assay result showed that, whereas Ani9 and the [Chemical Formula 27] compound exhibited an insignificant effect of inhibiting the cell viability of the PC-3 cells highly expressing ANO1 and the PC3 cells not expressing ANO1, the [Chemical Formula 5] compound selectively inhibited the growth of the PC-3 cells highly expressing ANO1 in a concentration-dependent manner.

Test. Example.4 Investigation of the Plasma Stability of the [Chemical Formula 5] Compound, and the Effect of [Chemical Formula 5] on Protein Level of ANO1 in PC-3 Cells FIG. 3A shows the stability of Ani9 and the [Chemical Formula 5] compound in mouse plasma, and FIG. 3B shows a western blot result of ANO1 in in PC-3 cells expressing ANO1 at high level.

Figure 3A:
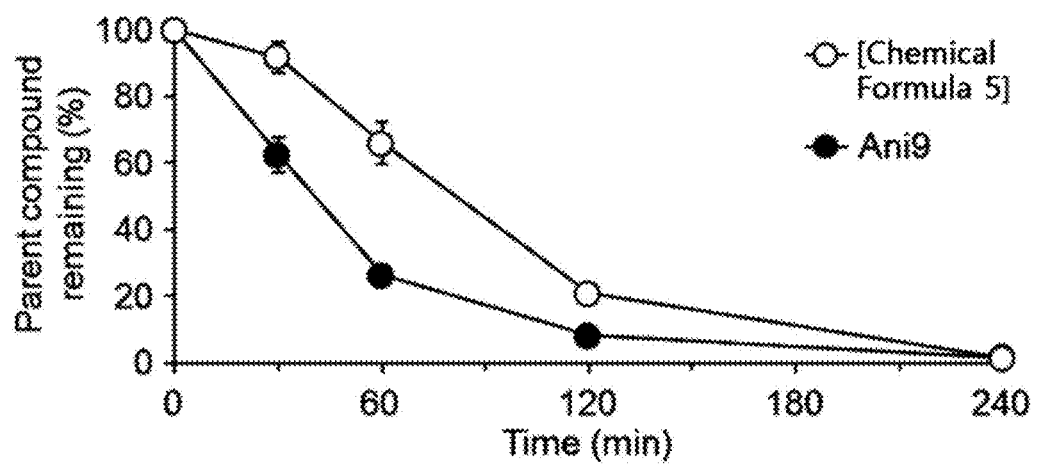
FIG. 3A shows the stability of Ani9 and a [Chemical Formula 5] compound in mouse plasma.

In FIG. 3A, after adding 5 μM of Ani9 or the [Chemical Formula 5] compound to mouse plasma, incubation was performed for 0, 30, 60, 120 or 240 minutes at 37° C. in a shaking incubator. Then, after precipitating proteins by centrifuging at 13,000 rpm for 10 minutes, only the supernatant was collected and the concentration of remaining Ani9 or [Chemical Formula 5] compound was measured by LC-MS/MS.

Figure 3B:
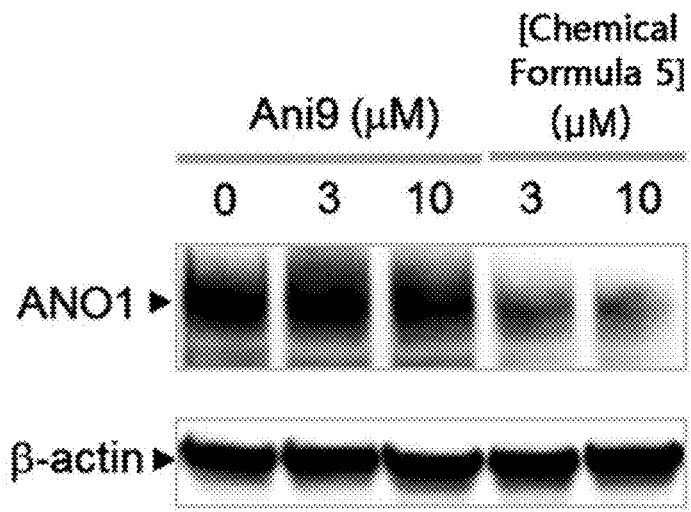
FIG. 3B shows a western blot result of ANO1 in PC-3 cells expressing ANO1 at high level.
Figure 3C:
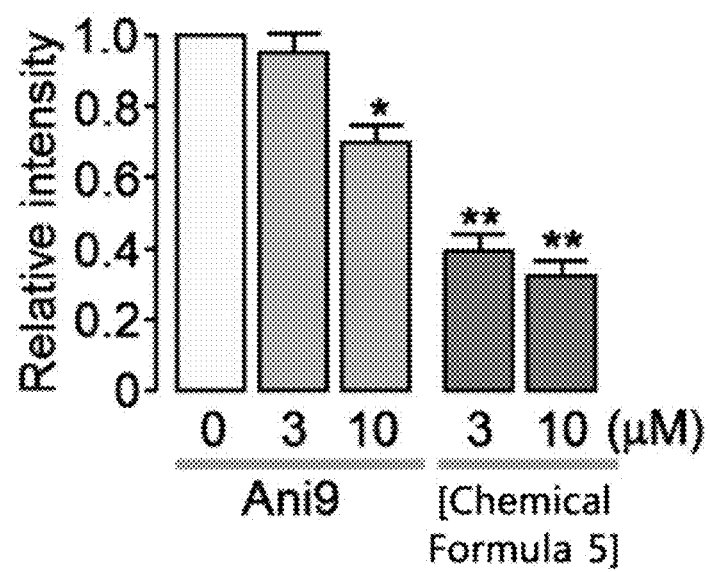
FIG. 3C shows a result of measuring the change in the expression level of the ANO1 protein in PC-3 cells expressing ANO1 at high level.

In FIG. 3B, PC3 cells highly expressing ANO1 were treated with Ani9 (3, 10 μM) or the [Chemical Formula 5] compound (3, 10 μM) and the change in the expression level of the ANO1 protein was measured by the western blot technique.

As seen from FIGS. 3A and 3B, the plasma stability of Ani9 was low, but the [Chemical Formula 5] compound showed higher stability in the mouse plasma than Ani9. Half-life was outstandingly long for the [Chemical Formula 5] compound (104 minutes) as compared to that for Ani9 (32 minutes).

In addition, it was confirmed that, whereas Ani9 (3, 10 μM) decreased the expression level of ANO1 in PC-3 cells (prostate cancer cells) expressing ANO1 by 5.2±6.3% and 29.2±3.4%, the [Chemical Formula 5] compound (3, 10 μM) decreased the expression level of ANO1 by 59.8±4.6% and 66.5±4.7%.

This reveals that the [Chemical Formula 5] compound (3, 10 μM) reduces the expression level of ANO1 about 11.5 times and 2.28 times as compared to Ani9.

As a result of the SAR assay, it was confirmed that some new compounds including the [Chemical Formula 5] compound ($IC_{50}$=22 nM) can be used as strong ANO1 inhibitors. Through selectivity analysis, it was confirmed that the [Chemical Formula 5] compound is very selective for ANO1, with 1,000 time or higher selectivity over ANO2.

This result suggests that the [Chemical Formula 5] compound is the strongest selective ANO1 inhibitor at present. The [Chemical Formula 5] compound was found to inhibit the proliferation PC-3 cells in a dose-dependent manner. In addition, it was confirmed that the [Chemical Formula 5] compound exhibits a very high effect of reducing the ANO1 protein as compared to Ani9 and shows superior plasma stability.

Figure 4A:
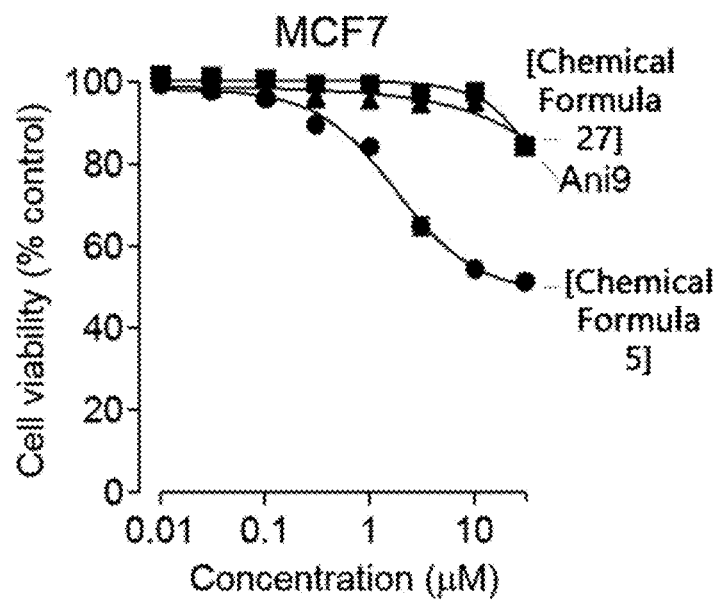
FIG. 4A shows a result of measuring the cell viability of MCF-7 (breast cancer cells) expressing ANO1 at high level depending on the concentration of Ani9, a [Chemical Formula 5] compound and a [Chemical Formula 27] compound.
Figure 4B:
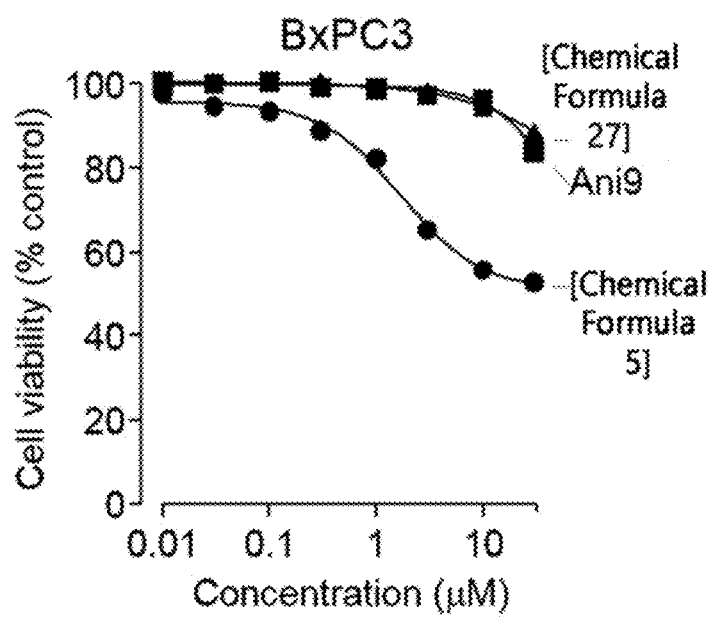
FIG. 4B shows a result of measuring the cell viability of BxPC3 (pancreatic cancer cells) expressing ANO1 at high level depending on the concentration of Ani9, the [Chemical Formula 5] compound and the [Chemical Formula 27] compound.

Test Example 5. Investigation of Effect of Inhibiting Growth of MCF7 Breast Cancer Cells and BxPC3 Pancreatic Cancer Cells of [Chemical Formula 5] Compound FIG. 4A shows a result of measuring the cell viability of MCF7 breast cancer cells expressing ANO1 at high level depending on the concentration of Ani9, the [Chemical Formula 5] compound and the [Chemical Formula 27] compound, and FIG. 4B shows a result of measuring the cell viability of BxPC3 pancreatic cancer cells expressing ANO1 at high level depending on the concentration of Ani9, the [Chemical Formula 5] compound and the [Chemical Formula 27] compound. The cell viability was determined by the MTS assay (mean±S.E., n=4).

In FIGS. 4A and 4B, MCF7 breast cancer cells and BxPC3 pancreatic cancer cells highly expressing ANO1 were cultured on a 96-well microplate, which about 5×10³ cells per each, and were treated with Ani9, the [Chemical Formula 5] compound or the [Chemical Formula 27] compound at different concentrations (0.01, 0.03, 0.1, 1, 3, 10, 30 μM). 24 hours later, after adding 20 μL of an MTS solution to each well and culturing at 37° C. for 30 minutes under 5% $CO_2$, absorbance was measured at 490 nm using a microplate reader.

As seen from FIGS. 4A and 4B, the MTS assay result showed that, whereas Ani9 and the [Chemical Formula 27] compound exhibited an insignificant effect of inhibiting the cell viability of the MCF7 breast cancer cells and BxPC3 pancreatic cancer cells highly expressing ANO1, the [Chemical Formula 5] compound selectively inhibited the growth of the MCF7 breast cancer cells and BxPC3 pancreatic cancer cells highly expressing ANO1 in a concentration-dependent manner.

Test Example 6. Investigation of Reducing ANO1 Protein Expressed in PC-3 Cells of [Chemical Formula 10] and [Chemical Formula 17] Compounds FIG. 5A shows a western blot result of ANO1 in PC-3 cells expressing ANO1 at high level depending on the concentration of Ani9, the [Chemical Formula 10] compound and the [Chemical Formula 17] compound, and FIG. 5B shows a result of treating PC3 cells expressing ANO1 at high level with Ani9 (10 μM), the [Chemical Formula 10] compound (10 μM) and the [Chemical Formula 17] compound (10 μM) and measuring the change in the expression level of the ANO1 protein by the western blot technique.

Figure 5A:
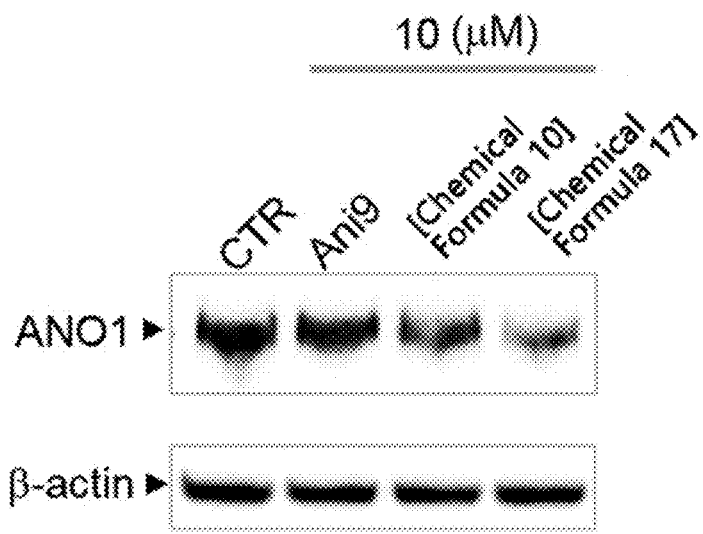
FIG. 5A shows a western blot result of ANO1 in PC-3 cells expressing ANO1 at high level depending on the concentration of Ani9, a [Chemical Formula 10] compound and a [Chemical Formula 17] compound.
Figure 5B:
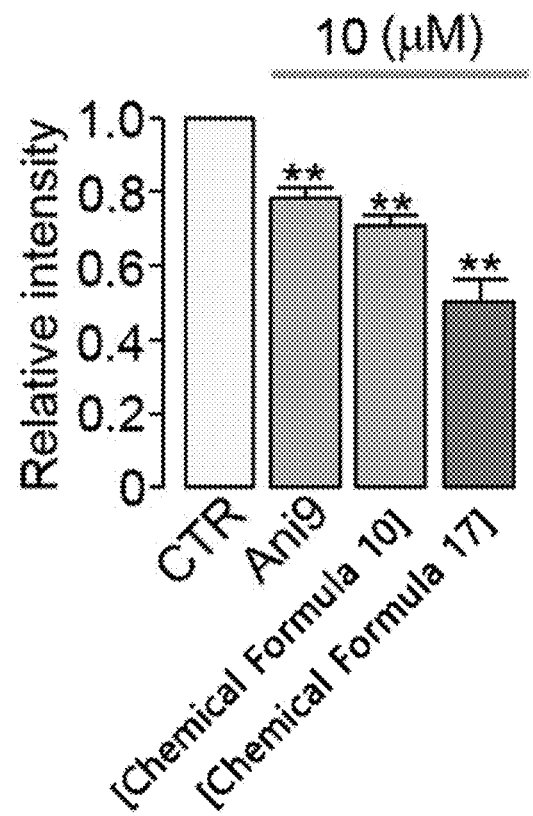
FIG. 5B shows a result of treating PC3 cells expressing ANO1 at high level with Ani9 (10 μM), the [Chemical Formula 10] compound (10 μM) and the [Chemical Formula 17] compound (10 μM) and measuring the change in the expression level of the ANO1 protein by western blot.

As seen from FIGS. 5A and 5B, whereas Ani9 (10 μM) decreased the expression level of ANO1 in PC-3 cells (prostate cancer cells) expressing ANO1 by 23.8±1.5%, the [Chemical Formula 10] compound (10 μM) and the [Chemical Formula 17] compound (10 μM) decreased the expression level of ANO1 by 28.9±0.9% and 48.8±2.9%, respectively.

This reveals that, although the [Chemical Formula 10] compound and the [Chemical Formula 17] compound (10 μM) exhibit relatively weaker effect of inhibiting the activity of the ANO1 than Ani9, they reduce the expression level of ANO1 by about 1.21 times and 2.05 times, respectively.

Test Example 7. Investigation of Effect of Inhibiting Contraction of Smooth Muscle by Chemical Formula 5] Compound FIG. 6A shows a result of measuring the effect of the [Chemical Formula 5] compound on the contraction of smooth muscle using mouse ileal section, FIG. 6B shows a result of measuring the effect of the [Chemical Formula 5] compound on the contraction frequency of smooth muscle, and FIG. 6C shows a result of measuring the effect of the [Chemical Formula 5] compound on the maximum contraction intensity of smooth muscle.

Figure 6A:
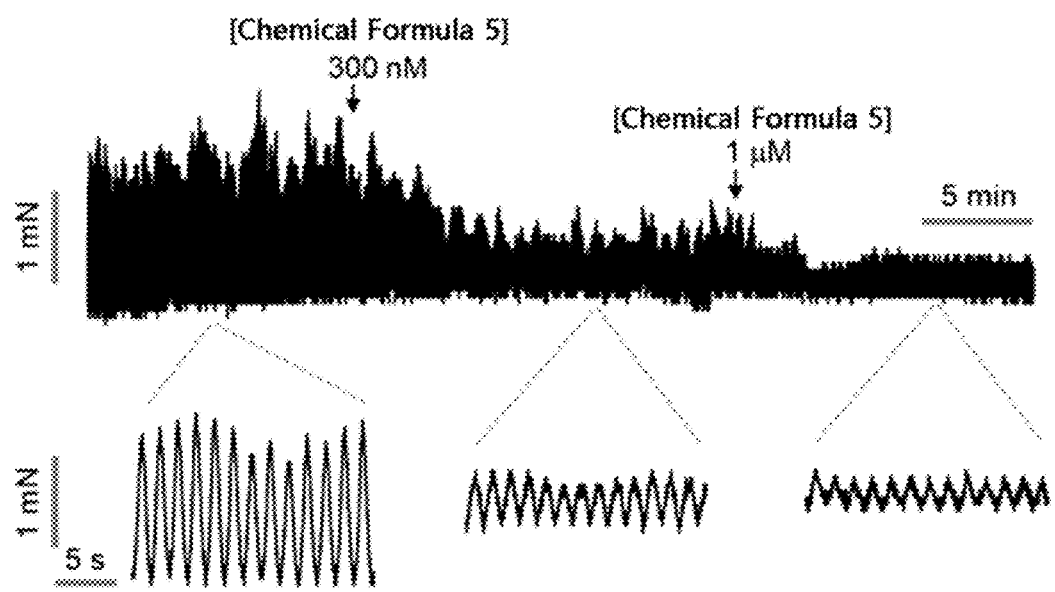
FIG. 6A shows a result of measuring the effect of a [Chemical Formula 5] compound on the contraction of smooth muscle using mouseileal section.
Figure 6B:
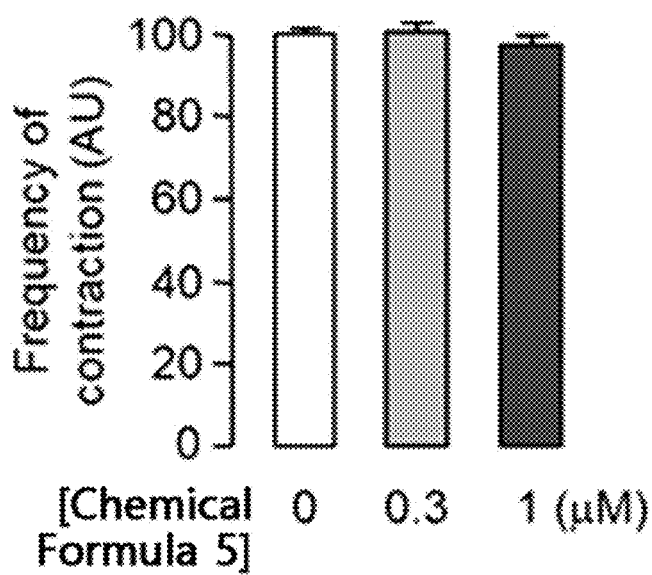
FIG. 6B shows a result of measuring the effect of a [Chemical Formula 5] compound on the contraction frequency of smooth muscle.
Figure 6C:
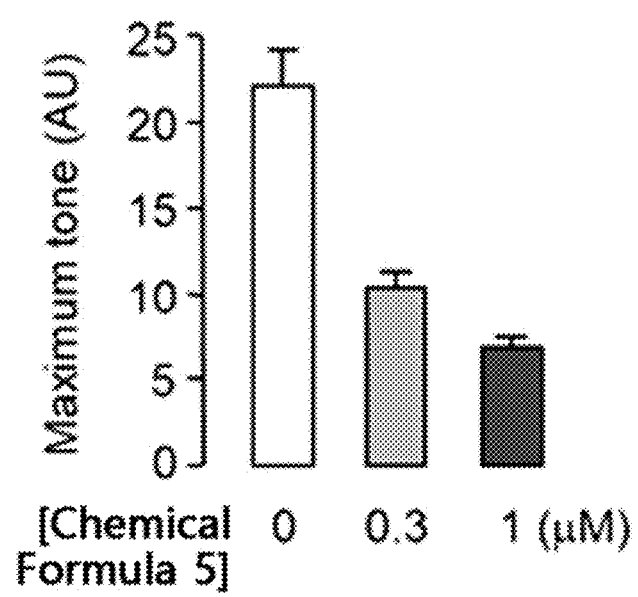
FIG. 6C shows a result of measuring the effect of a [Chemical Formula 5] compound on the maximum contraction intensity of smooth muscle.

As seen from FIG. 6A, the [Chemical Formula 5] compound strongly inhibited the contraction of smooth muscle of the mouse ileum in a concentration-dependent manner. Also, as seen from FIGS. 6B and 6C, it was confirmed that, whereas the [Chemical Formula 5] compound had no effect on the contraction frequency of smooth muscle, it decreased the maximum contraction intensity of smooth muscle by 53.3% and 68.8% at 300 nM and 1 μM, respectively.

This reveals that the [Chemical Formula 5] compound strongly inhibits the contraction of smooth muscle by inhibiting ANO1.

Accordingly, it can be used as a therapeutic agent for hypertension, which relaxes vascular smooth muscle, or as a therapeutic agent for asthma, which relaxes respiratory smooth muscle.

What is claimed is:

1. An anticancer pharmaceutical composition comprising a compound represented by [Chemical Formula 5]:

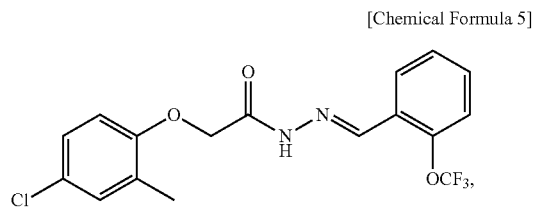 [SMILES: Cc1cc(Cl)ccc1OCC(=O)N/N=C/c1ccccc1OC(F)(F)F]

[Chemical Formula 5]

as an active ingredient.

2. The anticancer pharmaceutical composition according to claim 1, wherein the compound represented by Chemical Formula 5 has an $IC_{50}$ [μM] for ANO1 (TMEM16A) of 0.01-65.

3. The anticancer pharmaceutical composition according to claim 1, wherein the compound represented by Chemical Formula 5 has an $IC_{50}$ [μM] for ANO1 (TMEM16A) of 0.01-0.08.

* * * * *